US010219751B2

(12) United States Patent
Petersen et al.

(10) Patent No.: US 10,219,751 B2
(45) Date of Patent: *Mar. 5, 2019

(54) SYSTEMS AND METHODS FOR DETERMINING PHYSIOLOGICAL CHARACTERISTICS OF A PATIENT USING PULSE OXIMETRY

(71) Applicant: LIONSGATE TECHNOLOGIES, INC., Vancouver (CA)

(72) Inventors: Christian Leth Petersen, Burnaby (CA); John Mark Ansermino, Vancouver (CA); Guy Dumont, Vancouver (CA)

(73) Assignee: Lionsgate Technologies, Inc., Vancouver (CA)

( * ) Notice: Subject to any disclaimer, the term of this patent is extended or adjusted under 35 U.S.C. 154(b) by 905 days.

This patent is subject to a terminal disclaimer.

(21) Appl. No.: 14/602,165

(22) Filed: Jan. 21, 2015

(65) Prior Publication Data
US 2015/0133756 A1    May 14, 2015

Related U.S. Application Data

(63) Continuation of application No. 14/118,177, filed as application No. PCT/CA2012/000459 on May 14, 2012, now Pat. No. 8,958,859.

(Continued)

(51) Int. Cl.
*A61B 5/1455* (2006.01)
*A61B 5/00* (2006.01)
(Continued)

(52) U.S. Cl.
CPC .......... *A61B 5/6898* (2013.01); *A61B 5/0015* (2013.01); *A61B 5/0205* (2013.01);
(Continued)

(58) Field of Classification Search
CPC ................ H05B 39/02; H05B 33/0809; H05B 33/0815; H05B 33/0818; H05B 33/0806; H05B 37/02; A61B 5/1455; A61B 5/7288
See application file for complete search history.

(56) References Cited

U.S. PATENT DOCUMENTS

| 4,848,901 A | 7/1989 | Hood, Jr. |
| 5,349,952 A | 9/1994 | McCarthy et al. |

(Continued)

FOREIGN PATENT DOCUMENTS

| CN | 1662083 A | 8/2005 |
| WO | 2012155245 A1 | 11/2012 |

OTHER PUBLICATIONS

Office Action dated Mar. 22, 2016 issued on the corresponding Japanese application No. 2014-510621 with English translation.
Chinese Office Action dated Jul. 20, 2015 issued on corresponding Chinese Patent Application No. 2012800342830.
Huang, Chih-Chung et al., "Design and Implementation of a Smartphone-Based Portable Ultrasound Pulsed-Wave Doppler Device for Blood Flow Measurement", IEEE Transactions on Ultrasonics, Ferroelectrics, and Frequency Control, vol. 59, No. 1, Jan. 2012, pp. 182-188.

(Continued)

*Primary Examiner* — Eric Winakur
(74) *Attorney, Agent, or Firm* — Borden Ladner Gervais LLP; Geoffrey deKleine

(57) ABSTRACT

Methods, systems and related apparatus are provided to enable an electronic device to operate an external sensor comprising one or more emitters for emitting electromagnetic radiation of two different wavelengths and a detector for generating a response signal based on received electromagnetic radiation of the two different wavelengths connectable to an audio interface by applying a harmonic driving signal to a first contact and a second contact of the (Continued)

audio interface for driving the emitters of the external sensor, receiving the response signal at a third contact of the audio interface, demodulating and demultiplexing the response signal into a first wavelength response signal and a second wavelength response signal, analyzing the first and second wavelength response signals to determine one or more vital signs, and outputting the determined one or more vital signs.

1 Claim, 18 Drawing Sheets

Related U.S. Application Data

(60) Provisional application No. 61/486,802, filed on May 17, 2011.

(51) Int. Cl.
*A61B 5/024* (2006.01)
*A61B 5/0205* (2006.01)

(52) U.S. Cl.
CPC ...... *A61B 5/02416* (2013.01); *A61B 5/14552* (2013.01); *A61B 5/6826* (2013.01); *A61B 5/7228* (2013.01); *A61B 5/7278* (2013.01); *A61B 5/0004* (2013.01); *A61B 5/02433* (2013.01); *A61B 5/746* (2013.01); *A61B 2560/045* (2013.01); *A61B 2562/227* (2013.01)

(56) References Cited

U.S. PATENT DOCUMENTS

| | | | |
|---|---|---|---|
| 5,735,285 | A | 4/1998 | Albert et al. |
| 5,800,348 | A | 9/1998 | Kaestle |
| 6,685,633 | B2 | 2/2004 | Albert et al. |
| 6,790,178 | B1 | 9/2004 | Mault et al. |
| 7,221,971 | B2 | 5/2007 | Diab et al. |
| 8,188,869 | B2 | 5/2012 | Wangrud |
| 8,301,232 | B2 | 10/2012 | Albert et al. |
| 2004/0220487 | A1 | 11/2004 | Vyshedskiy et al. |
| 2006/0121590 | A1* | 6/2006 | Speerli ............... C12M 35/02 435/173.1 |
| 2008/0033265 | A1 | 2/2008 | Diab et al. |
| 2008/0077026 | A1 | 3/2008 | Banet et al. |
| 2010/0113950 | A1 | 5/2010 | Lin et al. |
| 2010/0287001 | A1 | 11/2010 | Pearce et al. |
| 2011/0015496 | A1 | 1/2011 | Sherman et al. |
| 2011/0082711 | A1 | 4/2011 | Poeze et al. |
| 2011/0273309 | A1 | 11/2011 | Zhang et al. |
| 2011/0301435 | A1 | 12/2011 | Albert et al. |
| 2011/0301439 | A1 | 12/2011 | Albert et al. |
| 2012/0071776 | A1 | 3/2012 | Keithline et al. |
| 2012/0116184 | A1 | 5/2012 | Shieh |
| 2012/0123222 | A1 | 5/2012 | Chen et al. |
| 2012/0156933 | A1 | 6/2012 | Kreger et al. |
| 2012/0225645 | A1 | 9/2012 | Sivan |
| 2012/0258433 | A1 | 10/2012 | Hope et al. |
| 2012/0302853 | A1 | 11/2012 | Chen et al. |

OTHER PUBLICATIONS

Booth, Jeremy, "A Short History of Blood Pressure Measurement", Section of the History of Medicine, vol. 70 Nov. 1977, pp. 793-799.
Edwards, Jocelyn, "Taking the pulse of pulse oximetry in Africa", Canadian Medical Association Journal, Feb. 15, 2012.
Fu, Tianyu, "Pulse Reading Mobile Application: Dr. Chi", Electrical Engineering and Computer Sciences University of California at Berkeley, UCB/EECS-2012-150, Jun. 1, 2012.
Adam, Jonathan et al., "iPhone Ultrasound", Final Report for ECE 445, Senior Design, May 2, 2012.
Oresko, Joseph, J. et al., "A Wearable Smartphone-Based Platform for Real-Time Cardiovascular Disease Detection Via Electrocardiogram Processing", IEEE Transactions on Information Technology in Biomedicine, vol. 14, No. 3, May 2010, pp. 734-740.
Lukkarinen, S. et al., "A New Phonocardiographic Recording System", Computers in Cardiology 1997, vol. 24, pp. 117-120.
Karlen, W. et al., "Human-centered phone oximeter interface design for the operating room: Pulse oximeter interfaced to a mobile device for anesthesia monitoring in the developing world", Proceedings of the International Conference on Health Informatics 2011, Jan. 26-29, 2011, pp. 433-438.
Khandoker, A.H. et al., "Smartphone-based low cost oximeter photoplethysmography", 6th International Conference on Electrical and Computer Engineering ICECE 2010, Dec. 18-20, 2010, pp. 634-637.
International Search Report dated Sep. 21, 2012 received in corresponding International Application PCT/CA2012/000459.
International Preliminary Report on Patentability dated May 10, 2013 received in corresponding International Application PCT/CA2012/000459.
Thomas A. Metzger et al. "2011 Capstone Design Awards: PulseLife: A Portable Pulse-Oximeter Monitor with Direct Audiojack Connection to Smartphone", Apr. 28, 2011.
Ashoka Reddy K et al. "Virtual Instrument for the Measurement of Haemo-dynamic Parameters Using Photoplethysmograph", IEEE Instrumentation and Measurement Technology Conference (IEEE Cat. No. 06CH37714C) IMTC, IEEE, Apr. 24, 2006.
Printout of "How to get electric power from head phone jack", stackoverflow.com, Apr. 6, 2011 (Apr. 6, 2011), XP055143047, Retrieved from the Internet: URL:http://stackoverflow.com/questions/556 0867/how-to-get-electric-power-from-head-p hone-jack [retrieved on Sep. 26, 2014] * the whole document *.
Extended European Search Report dated Oct. 17, 2014, issued in respect of corresponding European Patent Application No. 12785809.0.

\* cited by examiner

SYSTEMS AND METHODS FOR DETERMINING PHYSIOLOGICAL CHARACTERISTICS OF A PATIENT USING PULSE OXIMETRY

CROSS REFERENCE TO RELATED APPLICATIONS

This application is a continuation of U.S. patent application Ser. No. 14/118,177 filed Nov. 15, 2013, which is a US National Phase of PCT Application No. PCT/CA2012/000459 filed on May 14, 2012, which claims the benefit of priority of U.S. Provisional Patent Application No. 61/486,802 filed May 17, 2011, all of which are incorporated herein by reference.

FIELD

The present disclosure relates to systems and methods for determining physiological parameters of a patient using pulse oximetry.

BACKGROUND

Pulse oximetry is a diagnostic method that measures the proportion of oxygen-carrying molecules in the blood (called hemoglobin) that are actually carrying oxygen. This is known as oxygen saturation or $SpO_2$. A conventional pulse oximeter sensor shines two light beams of different wavelengths (e.g., red and infrared) through the blood that is circulating in the small blood vessels of an extremity (e.g., the finger or ear), and then detects the amount of light that is able to pass through the extremity. Hemoglobin carrying oxygen (red blood) absorbs more infrared light and allows more red light to pass than hemoglobin without oxygen (blue blood) which allows more infrared light to pass. The oxygen saturation is expressed as a percentage of hemoglobin that has oxygen attached to it. One hundred percent oxygen saturation is attained when all the hemoglobin in the blood is completely saturated with oxygen.

Oxygen is the source of life for all cells in the body. Oxygen is carried from the lungs to our cells by the blood. A short interruption in the supply of oxygen will kill cells, and a slightly longer interruption can kill the whole body. Hemoglobin in the blood is normally almost fully saturated with oxygen ($SpO_2$=95-100%). A decrease below this level indicates that either the amount of oxygen being delivered throughout the body is reduced or the amount being used by the body has increased. Pulse oximetry may be used to detect reduced levels of oxygen in the blood before the clinical sign of oxygen deprivation (skin turns blue) can be seen. This early detection of a reduced level of oxygen allows early rescue before levels of oxygen drop to critical levels. Pulse oximetry has contributed significantly to reducing the risk of death associated with anesthesia.

Since its introduction into the operating room in the 1980s, pulse oximetry has been routinely used to monitor patients who are under anesthesia during surgery. Its use has spread throughout the hospital so that any patient with unstable oxygen levels may be monitored, for example, in the intensive care unit, the emergency department or on the ward. Pulse oximetry can also be used at home by patients with lung disease.

Pulse oximetry has the potential to act as diagnostic device that can identify early signs of lung disease or as indicators of the severity of diseases that affect the whole body. Typically, $SpO_2$ decreases as these diseases progressively worsen, when the lungs begin to fail and the body's use of oxygen increases. A decrease in blood oxygen saturation ($SpO_2$), resulting from impeded gas exchange in the lungs, is a strong predictor of critical illness in pneumonia and other infectious or inflammatory diseases. Indeed, pneumonia diagnosis based on a low $SpO_2$ can differentiate severe from mild respiratory tract infections, such as the common cold.

Prior art diagnostic pulse oximeters are typically bulky (e.g. they may weigh over 2 kg with a large footprint) and expensive custom built devices that are not available in many locations where they might be clinically useful. The World Health Organization (WHO) estimates a shortage of 90,000-150,000 oximeters in hospitals worldwide for anesthesia.

In many prior art oximeters electrical waveform signals used to generate the oximeter sensor light beams are of a substantially rectangular nature. Rectangular waves contain a high sub-band content of harmonics of the fundamental frequency and this introduces artifacts in the measured signal in the form of noise aliasing. In particular, harmonics of the line frequency are difficult to eliminate. In addition, many prior art oximeters make use of time division multiplexing to analyze detected light signals which can introduce challenges to distinguish between light from the sensor emitters and spurious ambient light.

Further, in many prior art oximeters, alarms are based on fixed thresholds that typically do not account for patient demographics and intra-patient variability. Often the generated alarms are unreliable, and clinicians tend to consider them to be a distraction.

The inventors have determined a need for improved methods and systems for conducting pulse oximetry. The inventors have determined a particular need for methods and systems for conducting pulse oximetry which are low cost, accurate, and robust.

SUMMARY

One aspect provides a method for controlling an electronic device to operate an external sensor connectable to an audio interface of the electronic device, the audio interface comprising a plurality of contacts, the external sensor comprising one or more emitters for emitting electromagnetic radiation of two different wavelengths and a detector for generating a response signal based on received electromagnetic radiation of the two different wavelengths. The method comprises applying a harmonic driving signal to a first contact and a second contact of the audio interface for driving the emitters of the external sensor, receiving the response signal at a third contact of the audio interface, demodulating and demultiplexing the response signal into a first wavelength response signal and a second wavelength response signal, analyzing the first and second wavelength response signals to determine one or more vital signs, and outputting the determined one or more vital signs.

Another aspect provides a system for controlling an electronic device to operate an external sensor connectable to an audio interface of the electronic device, the audio interface comprising a plurality of contacts, the external sensor comprising one or more emitters for emitting electromagnetic radiation of two different wavelengths and a detector for generating a response signal based on received electromagnetic radiation of the two different wavelengths. The system comprises a driving signal generator configure to apply a harmonic driving signal to a first contact and a second contact of the audio interface for driving the emitters of the external sensor, a response signal demodulator and demultiplexer configured to receive the response signal from a third contact of the audio interface and demodulate and demultiplex the response signal into a first wavelength response signal and a second wavelength response signal, a response signal analyzer configured to analyze the first and second wavelength response signals to determine one or more vital signs, and an output configured to output the determined one or more vital signs.

Another aspect provides a method for generating a driving signal for an oximeter sensor comprising a red LED and an infrared LED connected in parallel with opposing polarities. The method comprises providing a base harmonic signal having a base amplitude less than an activation voltage of the red and infrared LEDs, and selectively providing periodic positive and negative triggering peaks in the base harmonic signal, the positive and negative triggering peaks having amplitudes greater than the activation voltage of the red and infrared LEDs.

Another aspect provides an oximeter sensor connectable to an audio interface of an electronic device comprising a connector configured to be received in the audio interface of the electronic device, the connector comprising a plurality of contacts, a pair of emitters configured to emit light of two different wavelengths, the pair of emitters connected in parallel with opposing polarities across a first contact and a second contact of the connector, and a detector configured to detect light of the two different wavelengths and generate a response signal comprising a first response signal component based on detected light from a first one of the pair of emitters and a second response signal component based on detected light from the other one of the pair of emitters, the detector connected to provide the response signal to a third contact of the connector.

Another aspect provides an adaptor for connecting an oximeter sensor to an audio interface of an electronic device, the adaptor comprising a first end having a jack plug comprising a plurality of contacts, the jack plug configured to be received in an audio jack, a second end comprising a plurality of holes configured to receive a plurality of pins of a pin-type connector, and a plurality of conductors connected between the plurality of contacts and the plurality of holes.

Another aspect provides a system for determining the physiological parameters of a patient using pulse oximetry. The system comprises an emitter for irradiating a blood filled body part of the patient with red electromagnetic radiation and infrared electromagnetic radiation, the red electromagnetic radiation and the infrared electromagnetic radiation modulated by a sinusoidal modulation signal, a detector for receiving an input signal comprising received red electromagnetic radiation and received infrared electromagnetic radiation that have passed through the body part, the received red electromagnetic radiation and the received infrared electromagnetic having a phase difference of 90 degrees, and a processor in electrical communication with the emitter and detector. The processor is configured to modulate the emitter with the modulation signal, receive the input signal from the detector, determine a first demodulation signal by quadrature demodulating the input signal using a first sinusoidal signal and a second sinusoidal signal each having the same frequency as the modulation signal, the first sinusoidal signal and second sinusoidal signal having a phase difference of 90 degrees, determine a second demodulation signal by quadrature demodulating the input signal using a third sinusoid signal and a fourth sinusoidal signal each having a frequency of twice the frequency as the modulation signal, the third sinusoidal signal and fourth sinusoidal signal having a phase difference of 90 degrees, determine the received red electromagnetic radiation based on a first linear combination of the first demodulation signal and second demodulation signal, determine the received infrared electromagnetic radiation based on a second linear combination of the first demodulation signal and second demodulation signal, and, determine physiological parameters of the patient based upon the received red electromagnetic radiation and the received infrared electromagnetic radiation.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides a method and system for controlling an external sensor such as an oximeter through an audio interface of an electronic device. Example embodiments are described herein with reference to hand held electronic devices such as smartphones or the like, but it is to be understood that the systems and methods described herein may be implemented in any type of electronic device with an audio interface and suitable signal generating and processing capabilities, including without limitation smartphones, feature phones, personal digital assistants, tablet computers, netbook computers, laptop computers, portable gaming systems, portable music players equipped with processors, desktop computers, or the like.

Figure 1:
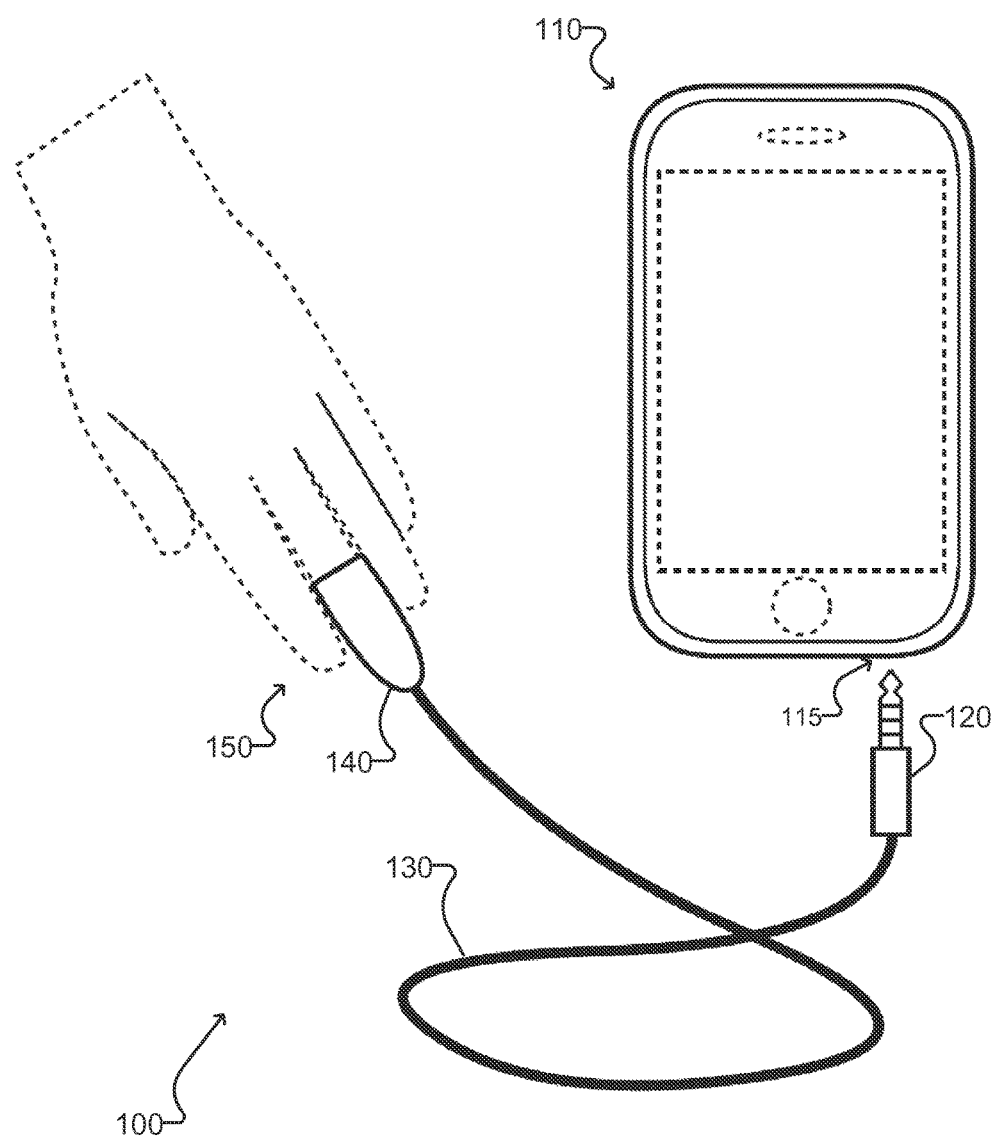
FIG. 1 is a diagram of an example portable diagnostic pulse oximetry system according to one embodiment.

Referring to FIG. 1, a portable diagnostic pulse oximetry system 100 is shown generally comprising a portable consumer electronic device 110, an oximeter sensor 140, a media connector 120, and an electrical cable 130. The portable consumer electronic device 110 generally comprises a media interface 115 (e.g., an audio interface), a processor, a memory, and various input/output means (such as, for example, a touch screen display, a display and a physical keyboard, etc.) In the illustrated embodiment, the portable consumer electronic device 110 is a mobile phone. Alternatively, device 110 may be any electronic device with an audio interface and suitable processing capabilities.

The oximeter sensor 140 generally comprises an emitter and a detector. The emitter generally functions to emit electromagnetic radiation at two different wavelengths (e.g. red and infrared light) through the body part 150 of the patient, while the detector generally functions to detect the electromagnetic radiation propagated through the body part 150. The oximeter sensor 140 can be attached to any available blood filled body part 150 of the patient, such as, for example, fingers, ears and toes. Alternatively the oximeter sensor 140 may be used in a reflective mode against the forehead or chest of the patient, or any other suitable body part in accordance with the practice of those skilled in the art.

In the illustrated embodiment, the emitter and detector are housed in an opaque enclosure configured to fit snugly around the finger 150 of the patient. The oximeter sensor enclosure may be comprised of silicone rubber, spring loaded polymeric material, combinations thereof, or any other suitable materials or combination of materials.

Device 110 is configured to perform a method for controlling media interface 115 to operate oximeter sensor 140. In particular, device 110 sends driving signals to the control the emitter of oximeter sensor 140 and processes response signals form the detector of oximeter sensor 140 to determine various vital signs, as described further below. In some embodiments, device 110 may be provided with computer executable instructions stored in memory which, when executed the processing elements of device 110, cause device 110 to execute such a method.

Figure 1A:
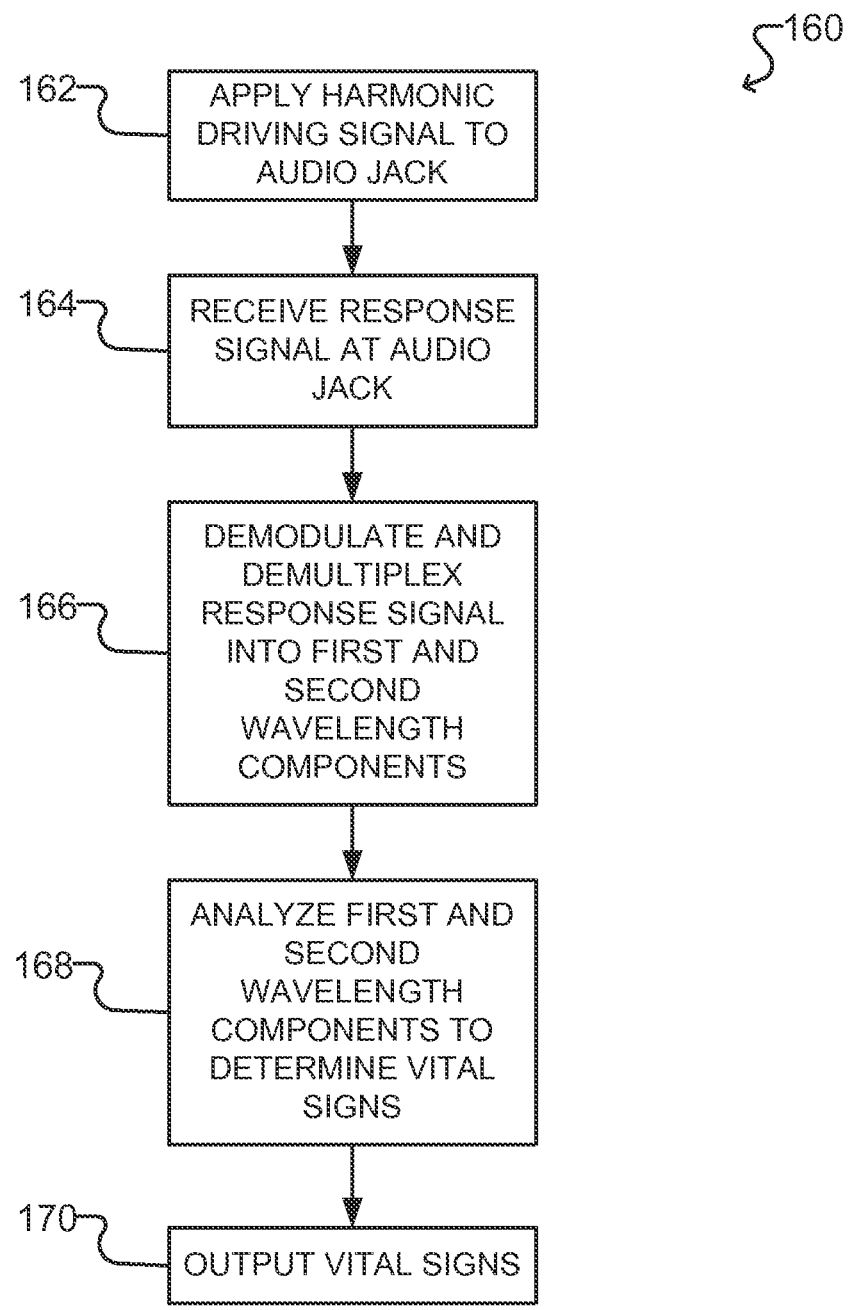
FIG. 1A is a flowchart illustrating an example method for controlling an electronic device to operate an external sensor connectable to an audio interface of the electronic device according to one embodiment.

FIG. 1A shows an example method 160 according to one embodiment. At block 162 a harmonic driving signal is applied to an audio interface of an electronic device to which an oximeter sensor is connected to cause the oximeter sensor to emit electromagnetic radiation of first and second wavelengths (e.g., red and infrared light). At block 164 a response signal from the oximeter sensor is received at the audio interface. The response signal comprises a first component corresponding to detected radiation of the first wavelength interlaced with a second component corresponding to detected radiation of the second wavelength. Example driving and response signals are described further below with reference to FIGS. 3, 9 and 10.

At block 166 the response signal is demodulated and demultiplexed to obtain the first and second components. As one skilled in the art will appreciate, the type of demodulation and demultiplexing preformed will depend on how the first and second components of the response signal are interlaced, which in turn depends on how the emitter of the oximeter sensor is driven by the driving signal. Example demodulation and demultiplexing schemes are described further below with reference to FIGS. 4 and 11.

At block 168 the first and second components of the response signal are analyzed to determine a variety of vital signs. For example, in some embodiments, oxygen saturation is determined from a ratio of the first and second components. In some embodiments a photoplethysmogram is obtained from the first and second components, and the photoplethysmogram is processed to determine other vital signs such as heart rate, respiratory rate, blood pressure and other physiological parameters as known in the art. At block 170 the vital signs are output to the patient and/or other user(s). For example, outputting the vital signs may comprise displaying the vital signs on a display of the electronic device, generating audible signals with built-in, speakers of the electronic device, storing the vital signs in memory of the electronic device, sending the vital signs to one or more other devices using any suitable communication protocols available at the electronic device, or any other form of output.

Figure 2:
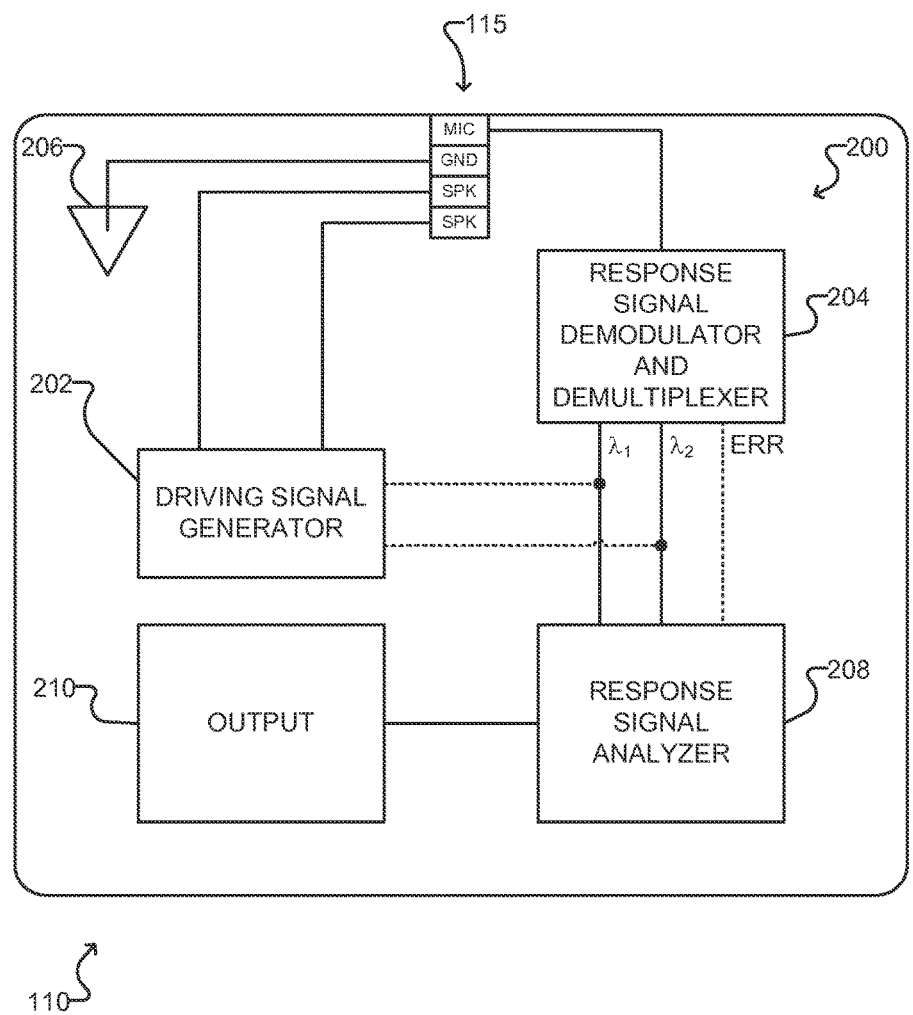
FIG. 2 schematically illustrates an example system for controlling an electronic device to operate an external sensor connectable to an audio interface of the electronic device according to one embodiment.

FIG. 2 shows an example system 200 according to one embodiment. System 200 may be implemented in an electronic device such as device 110 to control media interface 115 to operate the emitter of an oximeter sensor and process the response signals from the detector of the oximeter sensor. In the illustrated embodiment, media interface comprises a TRRS (tip, ring, ring, sleeve) audio interface wherein the tip and first ring comprise speaker contacts SPK, the second ring comprises a ground contact GND, and the sleeve comprises a microphone contact MIC, but it is to be understood that different types of audio interfaces may be used. For example, some embodiments may use a TRRS audio interface with a different arrangement of contacts. Some embodiments may use a pair of TRS type interfaces (e.g., a speaker output interface and a microphone input interface). Some embodiments may use differently configured audio interfaces with a plurality of contacts for sending and receiving electrical signals. In the illustrated embodiment, system 200 comprises a driving signal generator 202 for applying harmonic driving signals to speaker contacts SPK, and a response signal demodulator and demultiplexer 204 for receiving a response signal from microphone contact MIC and obtaining first and second wavelength components $\lambda_1$ and $\lambda_2$ therefrom, and provide first and second wavelength components $\lambda_1$ and $\lambda_2$ to a response signal analyzer 208, which determines one or more vital signs and provides the determined vital signs to output 210. An internal ground 206 is connected to ground contact GND.

In some embodiments response signal demodulator and demultiplexer 204 may also optionally determine an error signal ERR from the response signal, as indicated by the dotted line connecting response signal demodulator and demultiplexer 204 to response signal analyzer 208. For example, response signal demodulator and demultiplexer 204 may be configured to generate error signal ERR to indicate when the received response signal has unexpected characteristics (e.g., an amplitude, DC offset or frequency outside of an expected range), such that response signal analyzer 208 may disregard potentially spurious readings in first and second wavelength components $\lambda_1$ and $\lambda_2$. In some embodiments first and second wavelength components $\lambda_1$ and $\lambda_2$ may also optionally be provided to driving signal generator 202, as indicated by the dotted lines connecting first and second wavelength components $\lambda_1$ and $\lambda_2$ to driving signal generator 202, for use as feedback in controlling parameters of the harmonic driving signals, as described further below.

Figure 2A:
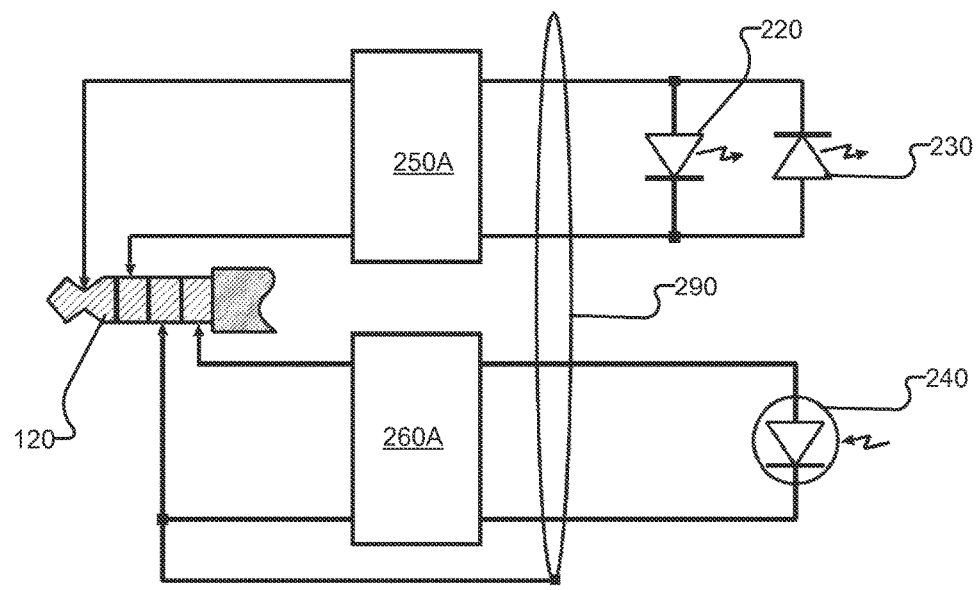
FIG. 2A schematically illustrates an example oximeter sensor according to one embodiment.
Figure 2B:
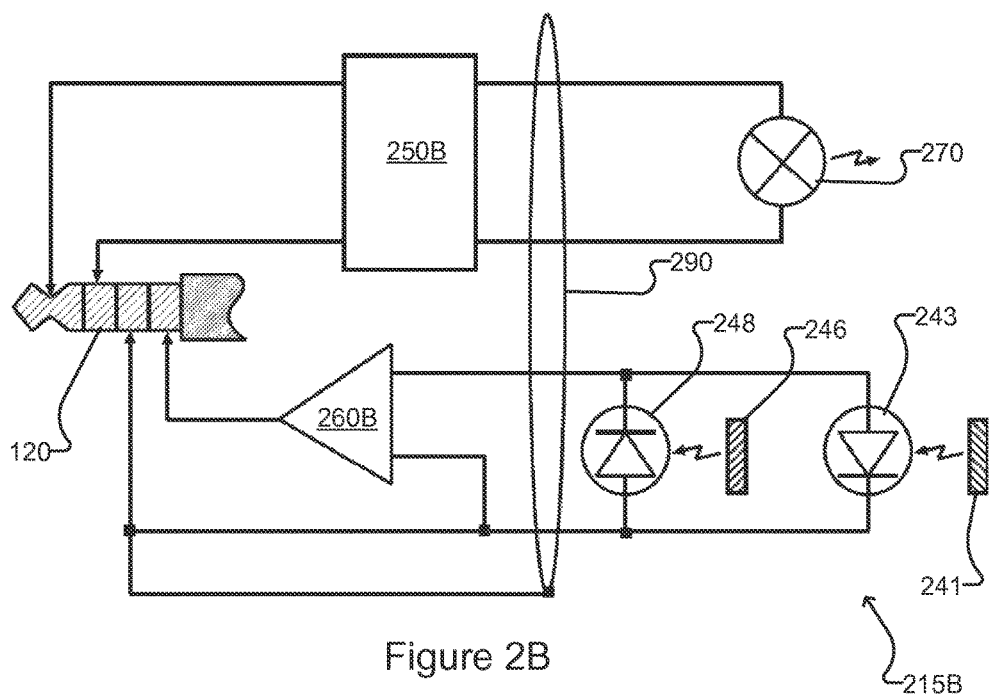
FIG. 2B schematically illustrates an example oximeter sensor according to one embodiment.

FIGS. 2A and 2B schematically illustrate two example oximeter sensors 215A and 215B which may be used as oximeter sensor 140 in system 100 of FIG. 1 and the electrical interface between the oximeter sensors 215A, 215B and the media connector 120 connectable to portable consumer electronic device 110 (see FIG. 1). In these embodiments, electrical signals are sent between the oximeter sensor 215A/215B and the portable consumer electronic device 110 through an electrical cable 130 and media connector 120. The electrical cable 130 is in electrical communication with the oximeter sensor 215A/215B and the media connector 120. The electrical cable 130 may be a multi-stranded electrical cable shielded in whole or in part by grounded conductor 290. The media connector 120 is configured to interface in electrical communication with any suitable media interface 115 available on a portable consumer electronic device 110, such as, for example, an audio interface. For example, the media connector 120 may be a 2.5 mm or 3.5 mm tip-ring-ring-sleeve (TRRS) connector configured to interface with an audio interface of a portable consumer electronic device 110. In other embodiments different media connectors may be used, such as, for example, a pair of tip-ring-sleeve (TRS) connectors for connection to speaker and microphone interfaces, or other types of connectors configured to connect to other types of audio interfaces. In the alternative, an oximeter sensor may be provided with means to communicate audio signals to and from the portable consumer electronic device 110 using any wired or wireless communication medium, method or protocol known in the art, such as, for example and without limitation, Bluetooth™, infrared, near field communication, and WiFi.

In the embodiment shown in FIG. 2A, the oximeter sensor 215A comprises two electromagnetic radiation emitters 220 and 230 configured to emit electromagnetic radiation at two different wavelengths being substantially in the red (600-700 nm wavelength) and infrared (800-1000 nm wavelength) regime, respectively. The emitters 220 and 230 may be Light Emitting Diodes (LEDs) or any other emitters capable of emitting red and infrared electromagnetic radiation known to those skilled in the art. The emitters 220 and 230 are connected in parallel with opposing polarities such that in operation one emitter 220 will be activated by positive driving signals while the other emitter 230 will be activated by negative driving signals. The oximeter sensor 215A also comprises an electromagnetic radiation detector 240 configured to be sensitive in the emission range of the emitters 220 and 230. The detector 240 may be a photo diode, photo transistor, photo sensitive resistor or any other suitable electromagnetic radiation detector.

The emitters 220 and 230 are electrically connected to a signal conditioning and filtering element 250A, while the detector 240 is electrically connected to a signal conditioning and filtering element 260A. The signal conditioning and filtering elements 250A and 260A may comprise any combination of resistive, capacitive, inductive and active electrical components necessary to achieve a desired signal conditioning and filtering.

In the embodiment shown in FIG. 2B, the oximeter sensor 215B comprises an electromagnetic radiation emitter 270 configured to emit electromagnetic radiation in both red and infrared regimes. The emitter 270 can be a miniature incandescent bulb, or any other wide bandwidth emitter of electromagnetic radiation known to those skilled in the art. The oximeter sensor 2156 also comprises two electromagnetic radiation detectors 243 and 248 configured to be sensitive to red and infrared radiation, respectively. The selective sensitivity of the detectors 243 and 248 may be intrinsic to the detectors, or may be achieved by electromagnetic radiation filters 246 and 241, or both. The filters 246 and 241 may be made of glass, plastic, resin, gel, polyester, polycarbonate or any other suitable material, and may contain one or more layers of optical coatings and any other means for filtering electromagnetic radiation known to those skilled in the art.

In the illustrated embodiment, the detectors 243 and 248 comprise photo diodes connected in parallel with opposing polarities such that in operation one detector 243 will generate positive polarity response signals comprising one of red or infrared electromagnetic radiation and the other detector 248 will generate negative polarity response signals comprising the other of red or infrared electromagnetic radiation. In the alternative, the detectors 243 and 248 may comprise photo transistors, photo sensitive resistors or any other suitable electromagnetic radiation detector known in the art.

The emitter 270 is electrically connected to a signal conditioning and filtering element 250B, while the detectors 243 and 248 are electrically connected to a signal conditioning and filtering element 260B. The signal conditioning and filtering elements 250B and 260B may comprise any combination of resistive, capacitive, inductive and active electrical components necessary to achieve a desired signal conditioning and filtering. In the illustrated embodiment, the signal conditioning and filtering element 260B comprises an amplifier, such as, for example, an operational amplifier, field effect transistor, bipolar transistor or any other such amplifying element or combinations thereof known to those skilled in the art. The detectors 243 and 248 generate photo voltages or currents of opposing polarity and the amplifier 260B transmits the difference measurement to the media connector 120.

Figure 2C:
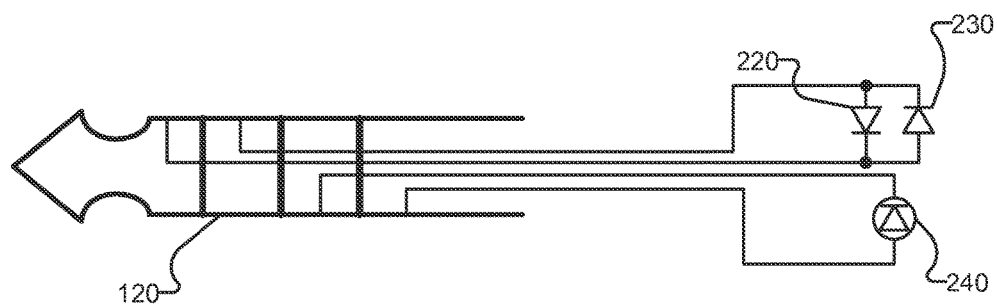
FIG. 2C schematically illustrates an example oximeter sensor according to one embodiment.

FIG. 2C schematically illustrates an example oximeter sensor 215C according to another embodiment which may be used as oximeter sensor 140 in system 100 of FIG. 1.

Oximeter sensor 215C is similar to sensor 215A of FIG. 2A in that it comprises two emitters 220 and 230 as described above connected in parallel with opposing polarities, and a single detector 240. However, sensor 215C differs from sensor 215A in that emitters 220 and 230 and detector 240 are directly connected to media connector 120.

Figure 2D:
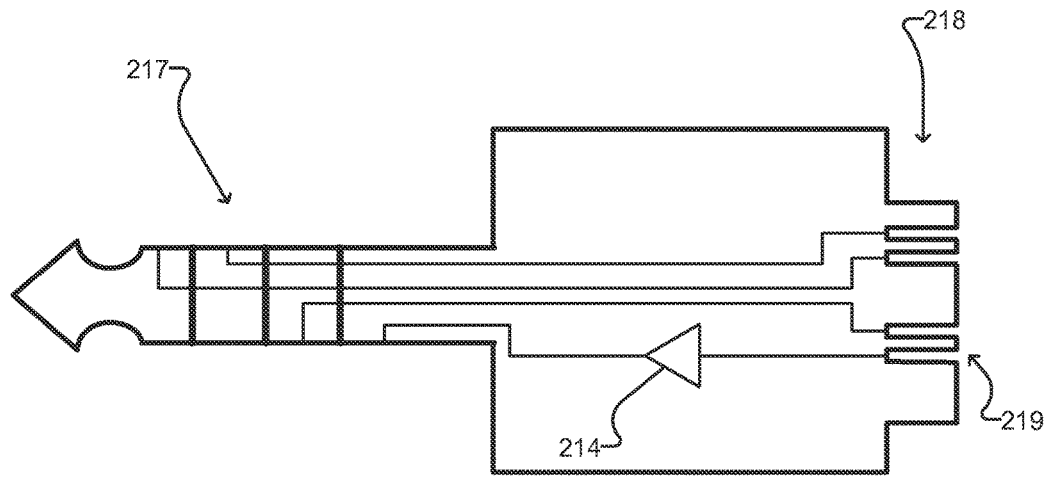
FIG. 2D schematically illustrates an example adaptor for coupling an oximeter sensor to an audio interface according to one embodiment.

FIG. 2D schematically illustrates an example oximeter sensor adaptor 216 according to one embodiment. Adaptor 216 comprises a first end 217 configured to connect to an audio interface of an electronic device, and a second end 218 configured to connect to a standard medical device interface (such as, for example, a D-sub 9 pin connector) coupled to an oximeter sensor. In particular, second end 218 comprises a plurality of holes 219 configured to receive pins of a medical device connector such that, when inserted into an audio interface, adaptor 216 provides an electrical connection between the contacts of the audio interface and the pins of the medical device connector. Adaptor 216 may also comprise a preamplifier 214 and optionally other signal conditioning elements. Preamplifier 214 (and any other signal conditioning elements) may, for example, be powered from the microphone contact of the audio interface in the same way as conventional electret microphones.

Figure 3:
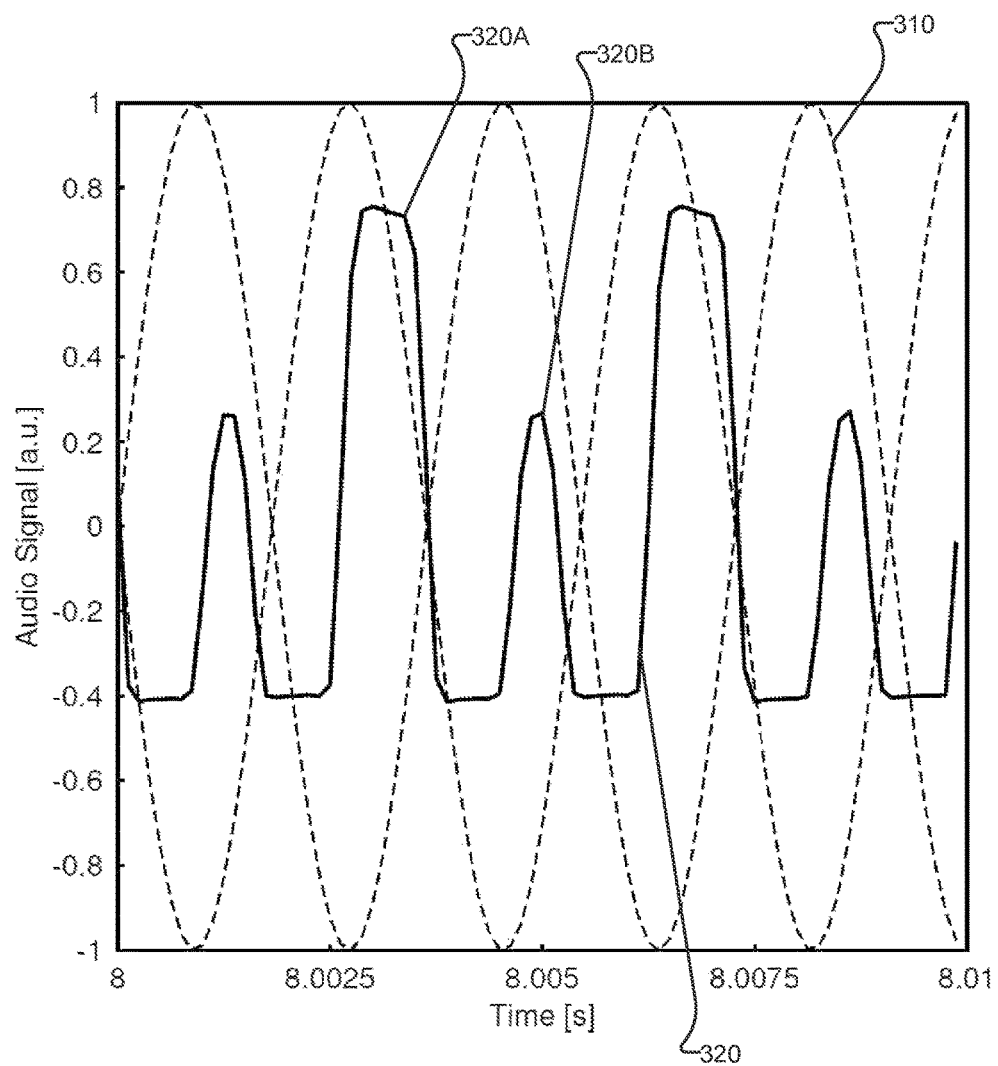
FIG. 3 is a graph of exemplary driving and response signals to and from an oximeter interface according to one embodiment.

FIG. 3 shows a graph of an example driving signal 310 which may be applied to contacts of an audio interface to drive emitters 220 and 230 of oximeter sensor 215A/215C shown in FIG. 2A/2C, as well as an example response signal 320 provided by the detector 240 of oximeter sensor 215A/215C shown in FIG. 2A/2C. The driving signal 310 is sinusoidal and stereophonic, the phase difference between the two output channels (e.g., the speaker contacts SPK shown in FIG. 2) being substantially 180 degrees. The response signal 320 is monophonic and contains alternating peaks 320A and 320B at twice the frequency of the driving signal, since the red and infrared emitters of the oximeter sensor activate on alternate polarities of the driving signal. The frequency of the driving signal 310 may, for example, be in the range of about 100-40,000 Hz. In the illustrated embodiment the frequency of the driving signal 310 is about 275 Hz.

Figure 4:
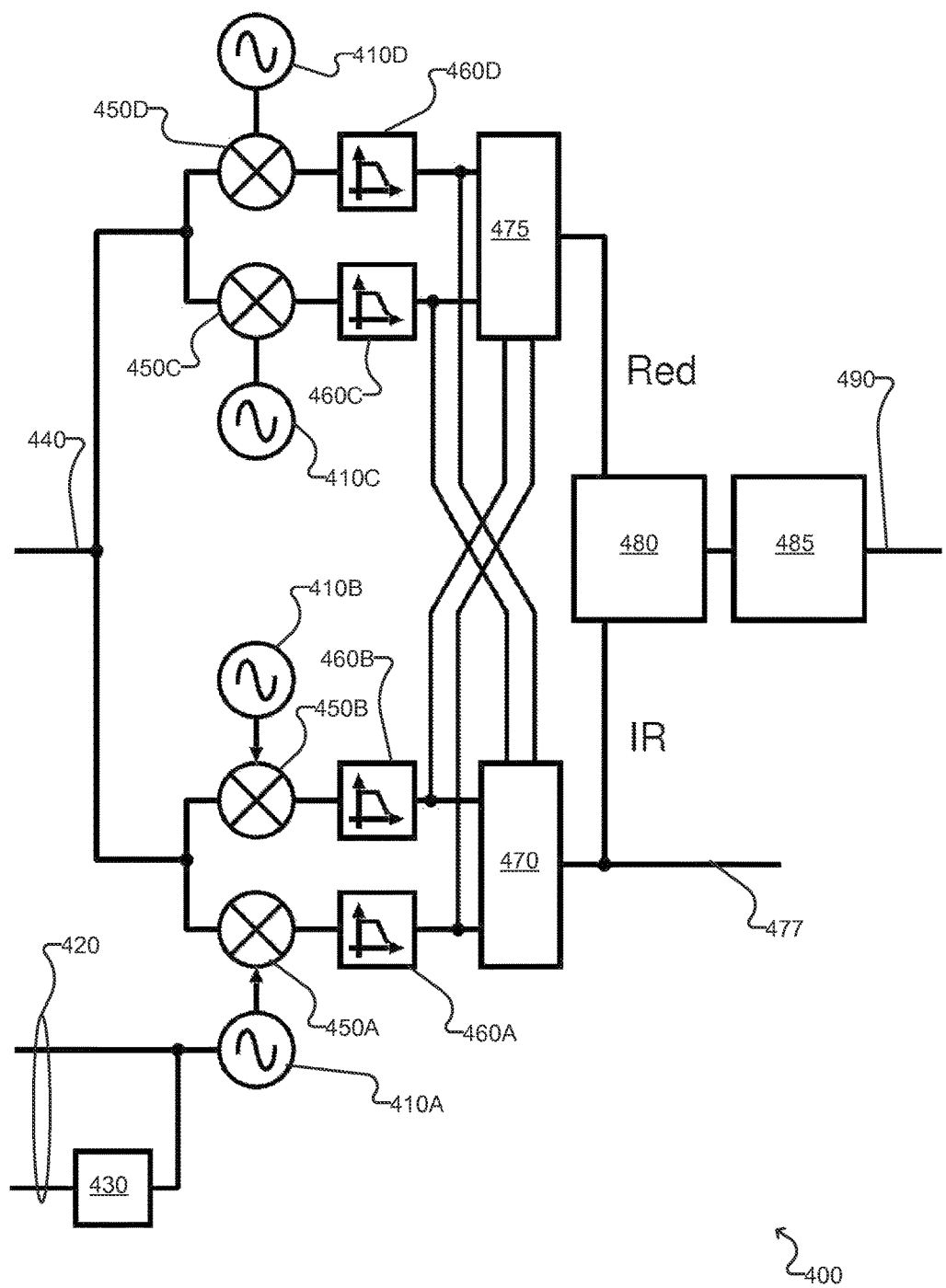
FIG. 4 is a functional diagram of an example system for generating oximeter driving signals and processing oximeter response signals according to one embodiment.

FIG. 4 shows a functional diagram of a system 400 for generating and processing oximeter signals such as the example signals 310 and 320 of FIG. 3. A stereophonic driving signal applied to outputs 420 (which may, for example, be connected across speaker contacts SPK of an audio interface) is generated by harmonic oscillator 410A and phase shifted substantially 180 degrees by phase shifter 430 to generate driving signal 310, consisting of two sinusoidal signals of opposite polarity mathematically represented as:

$$O_1 = A\sin(\omega t), O_2 = -A\sin(\omega t) \tag{1}$$

where $O_1$ is the first sinusoidal signal, $O_2$ is the second sinusoidal signal, A is the amplitude of the signals, $\omega$ is the angular frequency, and t is time.

The output signal 420 is directed to the emitter(s) of the oximeter sensor 140 to irradiate the body part 150 of the patient. The incoming response signal generated by the detector(s) of the oximeter sensor 140 is received at input 440 (which may, for example, be connected to the microphone contact MIC of an audio interface). The response signal can be represented by positive sine half cycles of differing amplitude, mathematically represented as:

$$I = \{\tfrac{1}{2}I_{Red}(sq(\omega t)+1) + \tfrac{1}{2}I_{IR}(1-sq(\omega t))\}\sin(\omega t) \tag{2}$$

where I is the incoming response signal, $I_{Red}$ and $I_{IR}$ are the amplitudes of the signal from the detector corresponding to the detected red and infrared light (compare peaks 320A and 320B in FIG. 3), and $sq(\omega t)$ is a square waveform of Fourier expansion:

$$sq(u) = \frac{4}{\pi}\sum_{k=1}^{\infty}\frac{\sin((2k-1)u)}{2k-1} \tag{3}$$

Equation (2) can be simplified to:

$$I = \tfrac{1}{2}(I_{Red}+I_{IR})\sin(\omega t) + \tfrac{1}{2}(I_{Red}-I_{IR})sq(\omega t)\sin(\omega t), \tag{4}$$

Quadrature demodulation is performed on the response signal received at input 440 at angular frequencies $\omega$ and $2\omega$ using multipliers 450A-D, harmonic oscillators 410A-D, and low pass filters 460A-D. In particular, harmonic oscillator 410A is configured to generate a first sinusoidal signal at angular frequency $\omega$; harmonic oscillator 410B is configured to generate a second sinusoidal signal at angular frequency w and having a 90 degree phase difference from the first sinusoidal signal; harmonic oscillator 410C is configured to generate a third sinusoidal signal at angular frequency $2\omega$; and harmonic oscillator 410D is configured to generate a fourth sinusoidal signal at angular frequency $2\omega$ and having a 90 degree phase difference from the third sinusoidal signal.

The response signal received at input 440 is separately multiplied by each of the first, second, third and fourth sinusoidal signals by multipliers 450A-D, respectively. The multiplied first, second, third and fourth sinusoidal signals are then filtered by low pass filters 460A-D, respectfully, to eliminate higher frequency harmonics, yielding:

$$I_\omega = \frac{1}{4}(I_{Red} + I_{IR}) \tag{5}$$

$$I_{2\omega} = \frac{1}{2\pi}(I_{Red} - I_{IR}) \tag{6}$$

where $I_\omega$ is the amplitude of the filtered multiplied first and second sinusoidal signals and $I_{2\omega}$ is the amplitude of the filtered multiplied third and fourth sinusoidal signal.

The amplitudes of the signals from each electromagnetic emitter, $I_{Red}$ and $I_{IR}$, are then determined at blocks 470 and 475, respectively, by solving the following linear combinations of $I_\omega$ and $I_{2\omega}$:

$$I_{Red} = 2I_\omega + \pi I_{2\omega} \tag{7}$$

$$I_{IR} = 2I_\omega - \pi I_{2\omega} \tag{8}$$

By relying on the magnitudes of the demodulated signals at frequencies $\omega$ and $2\omega$ and the linear combinations provided in Equations (7) and (8), the arbitrary phase shifts that typically occur between the driving and response signals of the system need not be determined. By contrast, demodulation at a single frequency would involve an orthogonal decomposition that typically can only be performed if the phase shift is known. The phase shift between the driving and response signals of a system depends on many factors, such as, the specific implementation of the audio interface, the temperature and system settings.

Figure 5:
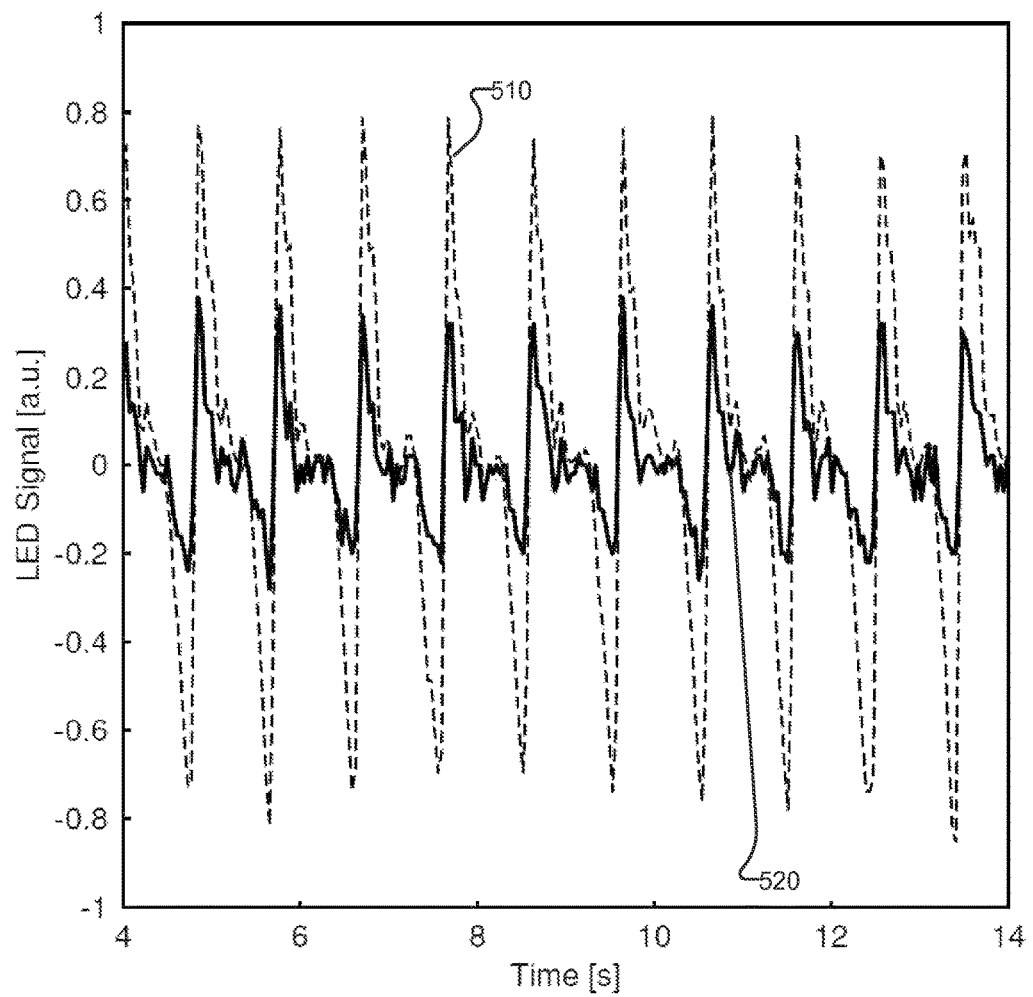
FIG. 5 is a graph of exemplary plethysmograms obtained from a system such as the example system of FIG. 4.

Referring to FIG. 5, an example graph of the real-time variation of $I_{Red}$ and $I_{IR}$ are shown as signals 520 and 510, respectively. These plethysmograms may be processed further to extract physiological parameters such as heart rate, respiratory rate, blood pressure, and any other physiological parameters of a patient. The processing may be performed using peak detection, frequency domain transforms, time domain analysis or any other technique known to those skilled in the art, or combinations thereof.

Referring back to FIG. 4, the direct current (DC) component of each waveform, $I_{Red}$ and $I_{IR}$, is determined in block 480 by standard signal processing methods, such as, for example, low pass filtering. The uncalibrated oxygen saturation ratio is then derived as:

$$R = \frac{AC_{red}/DC_{red}}{AC_{infrared}/DC_{infrared}} \quad (9)$$

where R is the uncalibrated oxygen saturation ratio, $DC_{red}$ is the DC component of the $I_{Red}$ waveform, $AC_{red}$ is $I_{Red}$–$DC_{red}$, and $DC_{infrared}$ is the DC component of the $I_{IR}$ waveform and $AC_{infrared}$ is $I_{IR}$–$DC_{infrared}$. Alternatively, any other similar relation known in the art may be used to determine the uncalibrated oxygen ratio.

In block 485 the oxygen saturation is determined by:

$$SpO_2 = f(R) \quad (10)$$

where $SpO_2$ is the oxygen saturation and f is a calibration function as known in the art. For example, in some embodiments f may be substantially linear such that f(R)=a–bR, where a and b are tabulated calibration constants. The oxygen saturation obtained in block 485 is provided to an output 490. The $I_{IR}$ waveform may also be provided to an output 477 connected to other elements for further processing, such as for example a peak detection block for determining heart rate bases on peaks in the $I_{IR}$ waveform.

Figure 6:
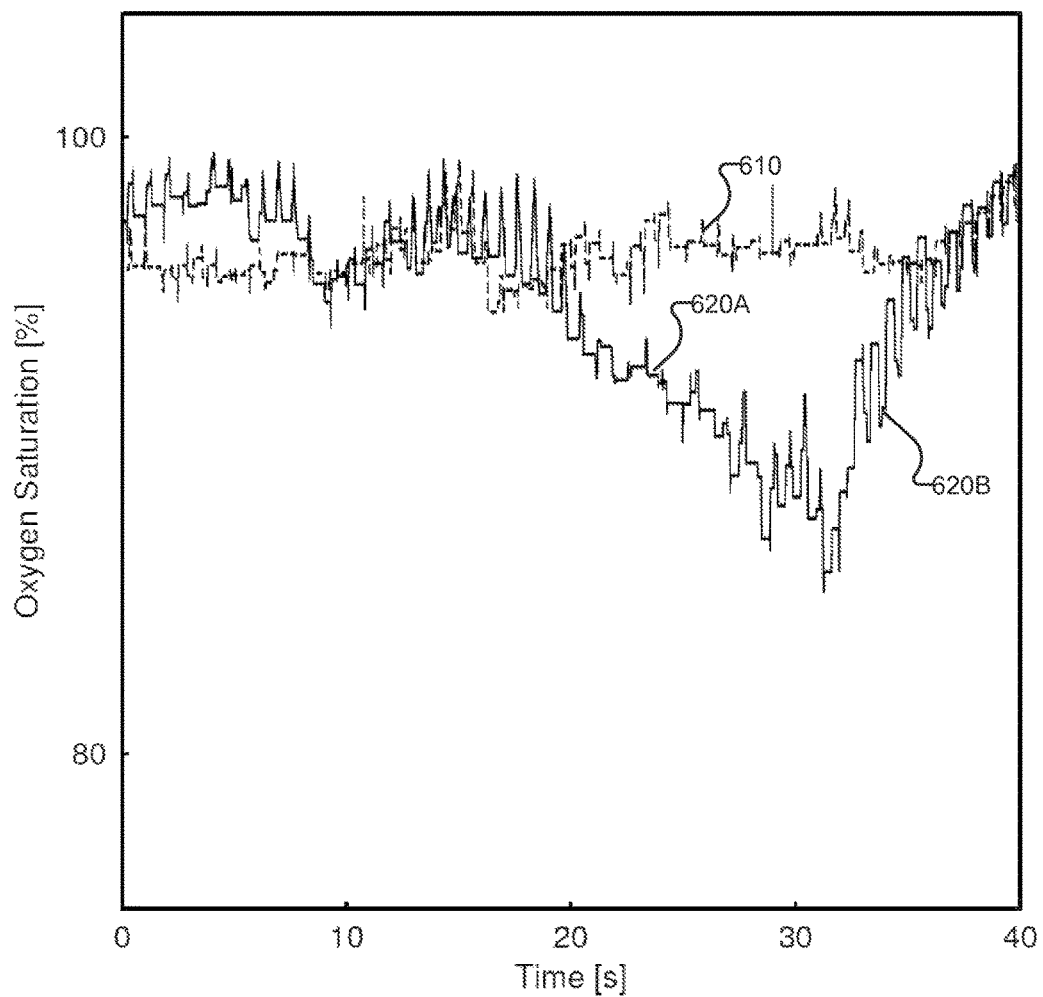
FIG. 6 is a graph of an exemplary raw oxygen saturation signal obtained from a system such as the example system of FIG. 4.

FIG. 6 shows an exemplary graph illustrating the raw oxygen saturation output of the system for processing oximeter signals described above with reference to FIG. 4. The oxygen saturation in a patient breathing normally is indicated at 610 is stable and near 100%. When deprived of oxygen the saturation drops significantly as indicated at 620A and increases back to the normal level when oxygen supply returns as indicated at 620B. The waveform spikes shown in this graph are artifacts that can be removed by standard filtering methods known in the art.

Figure 7:
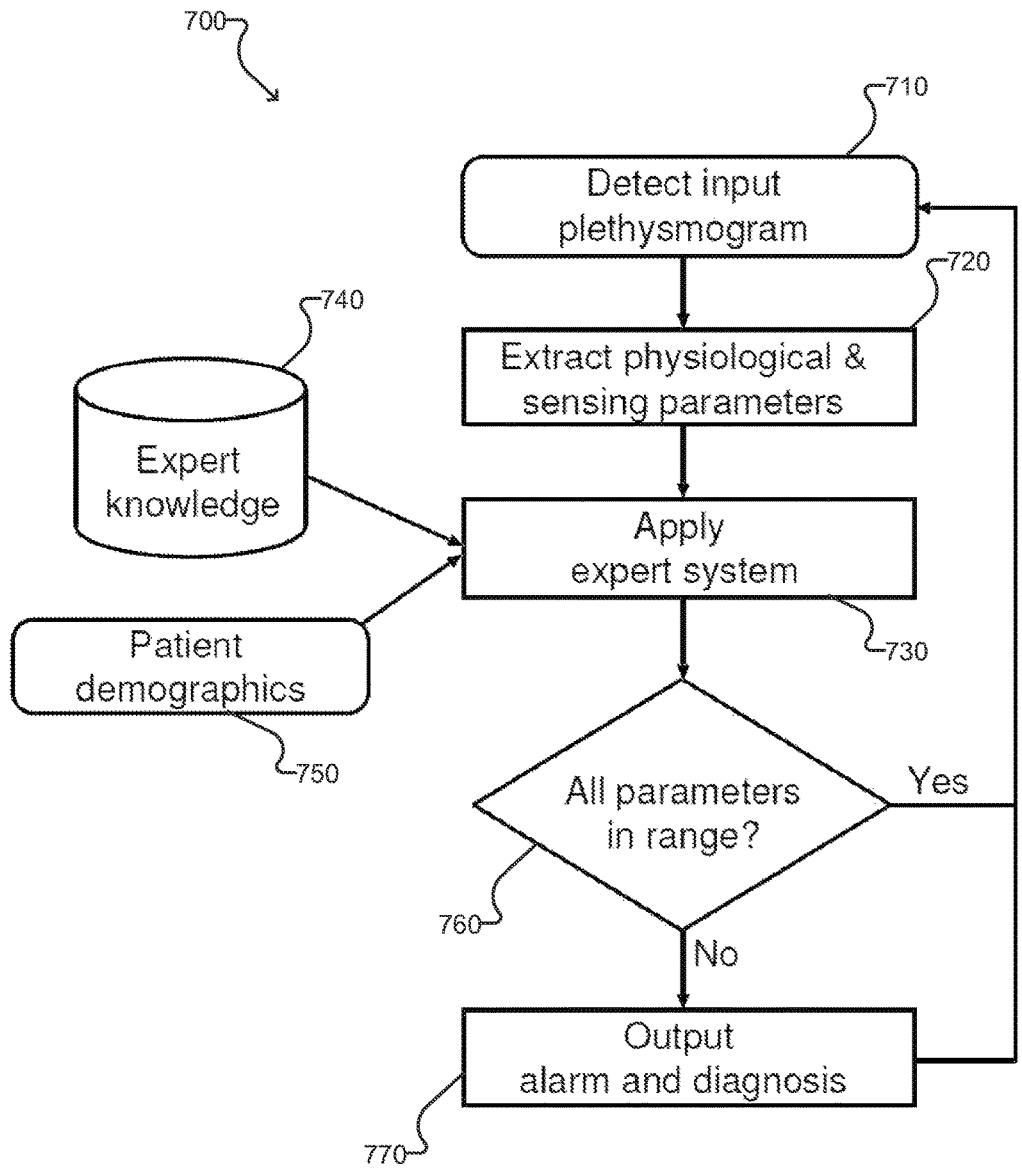
FIG. 7 is a flowchart illustrating an example method for generating alarms and diagnostic messages according to one embodiment.

FIG. 7 shows a functional diagram of an example method 700 for generating alarms and diagnostic messages according to one embodiment. In block 710, input plethysmograms as shown in FIG. 5 are obtained using a system such as system 400 for processing oximeter signals described above with reference to FIG. 4. In block 720, the plethysmogram signal is further processed to extract physiological trends such as oxygen saturation, heart rate, respiratory rate, blood pressure, and any other relevant physiological parameter, as well as signal quality measures.

In block 730, the extracted physiological parameters are input to an expert system which uses an expert knowledge database 740 and patient specific demographics 750 to determine the state of the patient. The expert system can be realized with any method known in the art, including forward chaining inference, neural nets, fuzzy logic, table lookups or combinations thereof. The expert knowledge database 740 is represented in a format compatible with the expert system, such as logic rule sets, network weights and data tables. The patient demographics 750 may be input through or stored in the portable consumer electronic device 110. Alternatively, the patient demographics 750 may be stored in and accessed from a remote system.

In block 760, it is determined whether the physiological parameters of the patient are within an acceptable range in consideration of the expert knowledge 740 and patient demographics 750. If the physiological parameters are within an acceptable range, the method returns to block 710 and continues to process oximeter sensor signals. If, however, the physiological parameters are outside of the accepted range, alarms and/or diagnostic information will be generated in block 770 based on the expert knowledge before further processing of oximeter sensor signals resumes. The alarm and diagnosis output may consist of audible, tactile, textural or iconic information and may be transmitted to or from a remote location using any remote communication capabilities of the portable consumer electronic device 110.

The example methods of processing oximeter signals described above may be performed entirely by the portable consumer electronic device 110, or partially by the portable consumer electronic device 110 and partially by a remote system. In particular, with the exception of the emission and detection of red and infrared electromagnetic radiation which is performed by an oximeter sensor, any of the method steps described above may be performed by the portable consumer electronic device 110 or a remote system. The portable consumer electronic device 110 and a remote system may communicate through and wired or wireless communication medium, method or protocol known in the art. Further, the remote system may comprise one or more remote servers, computers or other suitable processing devices.

Figure 8:
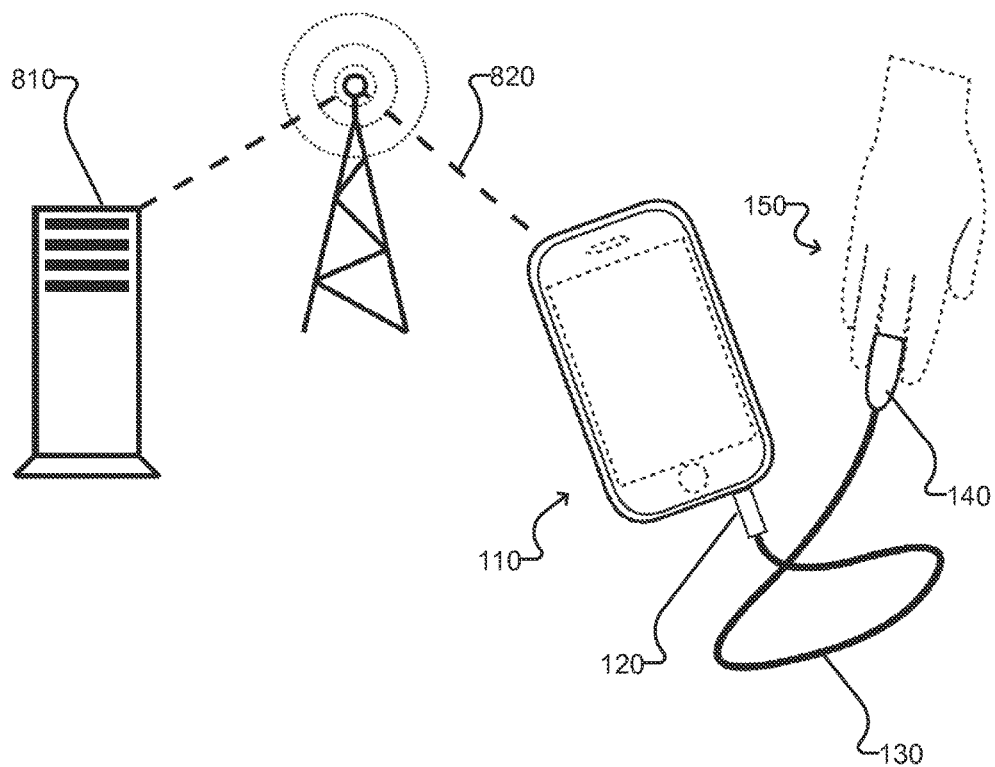
FIG. 8 schematically illustrates an example remote system in communication with a portable diagnostic pulse oximetry system according to one embodiment.

Referring to FIG. 8, an alternative embodiment is shown where the signal generating, analysis and diagnostic processing occur on a remote system 810. The remote system 810 communicates through wireless network 820 with the portable consumer electronic device 110, and the oximeter sensor 140 is driven and read through a standard voice audio telephone session, while demographics and diagnostic information is transmitted between the remote device 810 and the portable consumer electronic device 110 via a data protocol such as Short Message Service (SMS). The remote system may be any suitable processing system known in the art, such as, for example, a server.

In practical applications, when providing methods and systems for controlling an oximeter from a portable consumer electronic device, it is highly desirable to ensure that the sensor power consumption does not reduce the battery life of the device at a level that is detrimental to other, often primary, uses of the device. Since pulse oximetry sensors typically rely on two relatively high current light emitting diodes (LEDs), special care needs to be taken to conserve power.

Certain embodiments provide methods and systems for reducing the duty cycle of the driving signals provided to oximeter sensor. Example embodiments for use with oximeter sensors comprising a red LED and an infrared LED, identify which polarity of the signal triggers the infrared LED, and selectively reduce the amplitude of peaks of that polarity in comparison to peaks of the opposite polarity which trigger the red LED, as described further below. This is non-trivial due to the AC coupled nature of the audio interface.

Certain embodiments also advantageously provide the ability to dynamically control the amplitudes of the peaks of the driving signal which activate each LED in such a way that the DC level of the response signal remains substantially constant. This facilitates auto-dimming in the event of an empty sensor (thereby further conserving power) as well as eliminating effects of spurious non-linearities in the input signal channel, and simplifying the determination of the blood oxygen saturation.

Figure 9:
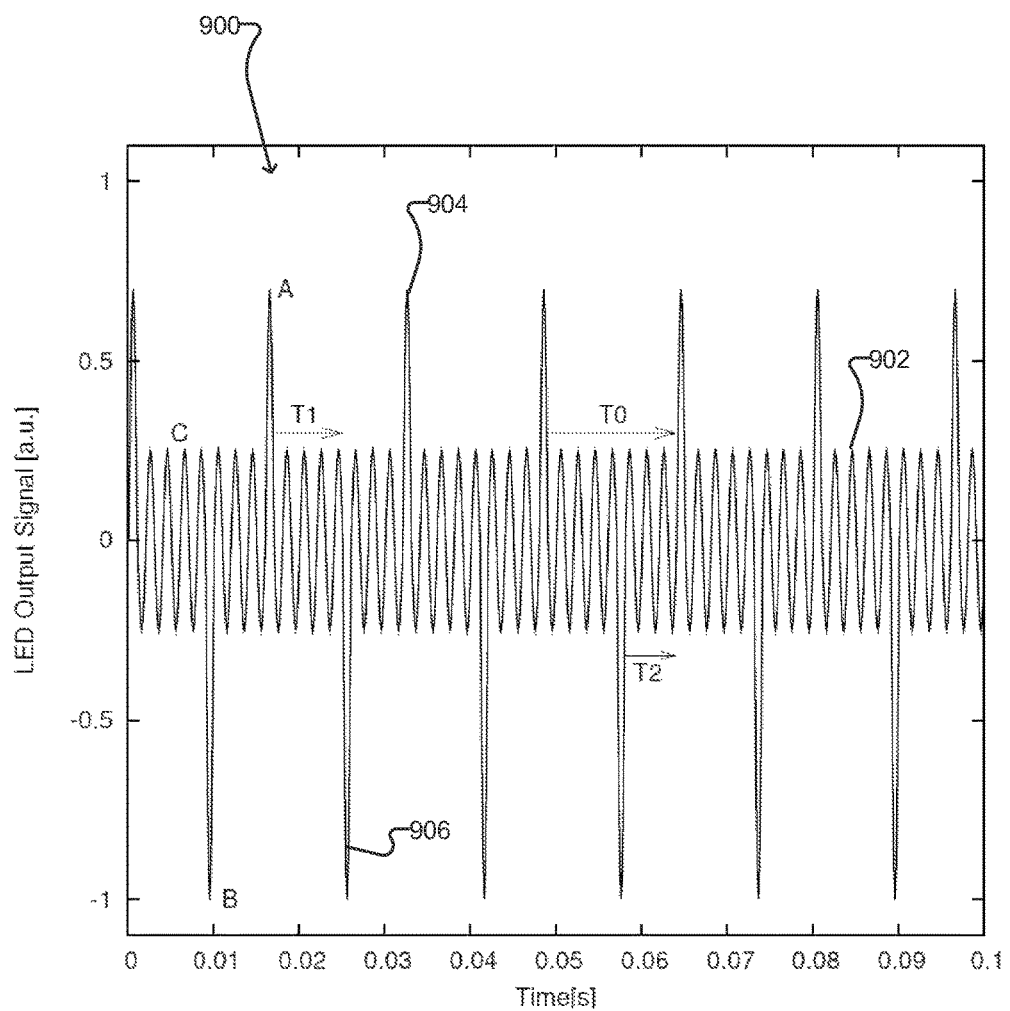
FIG. 9 is a graph of an exemplary driving signal for driving an oximeter sensor according to one embodiment.
Figure 10:
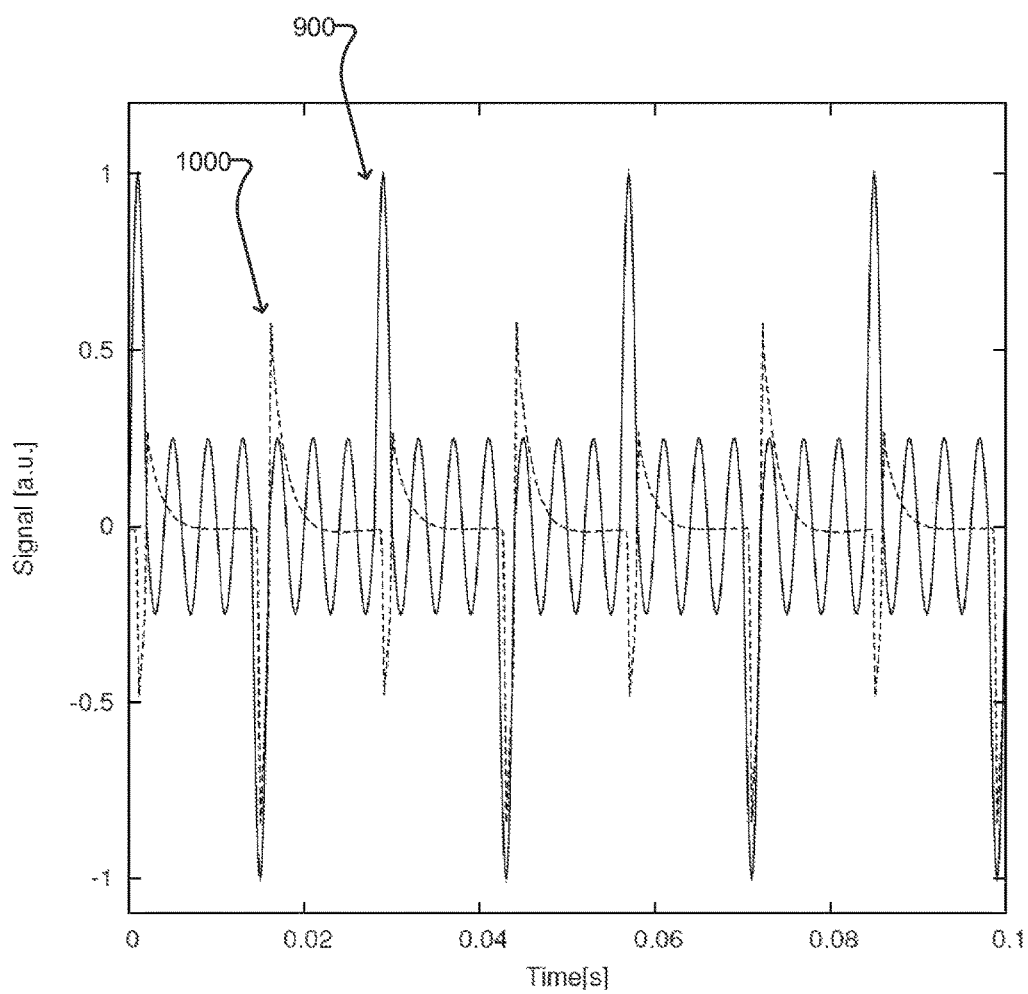
FIG. 10 is a graph showing an exemplary response signal overlayed on the exemplary driving signal of FIG. 9.

FIG. 9 shows an example driving signal 900 for controlling red and infrared LEDs of an oximeter sensor according to one embodiment. Signal 900 is configured for driving an oximeter sensor with an infrared LED connected to be activated by a positive polarity signal and a red LED connected to be activated by a negative polarity signal. Signal 900 comprises a base harmonic signal 902 with a plurality of periodic positive polarity triggering peaks 904 and negative polarity triggering peaks 906. The base harmonic signal 902 has an amplitude C that is in and of itself too small to activate the LEDs of the sensor, i.e. lower than the forward bias of the LEDs. Positive and negative peaks 904 and 906 have amplitudes A and B which are large enough to activate the respective LEDs, and these amplitudes may be adjusted independently. The base harmonic signal 902 may, for example have a frequency in the range of about 50-4000 Hz. In some embodiments the frequency of the base harmonic signal is about 500 Hz. Signal 900 has a period of T0, and the basic sampling frequency of the oximeter sensor is 1/T0. In some embodiments the positive and negative polarity triggering peaks 904 and 906 may each be provided in signal 900 at a frequency of 1/T0. In some embodiments, T0 may be selected such that 1/T0 is in the range of about 10-300 Hz. In some embodiments, T0 may be selected such that 1/T0 is about 30 Hz.

Signal 900 is generated in such a way that the positive and negative peaks 904 and 906 happen with same frequency, but offset by a certain number of half cycles of the base signal. In the illustrated example, T1 is the time from a positive peak 904 to a subsequent negative peak 906, and T2 is the time from a negative peak 906 to a subsequent positive peak 904. The difference between T1 and T2 can be readily detected in the response signal (see FIG. 10, which shows an example response signal 1000 overlaid atop driving signal 900) to identify which response signal peaks are associated with which wavelength of detected light. Since the infrared component of the response signal is generally higher than the red (due to a lower forward voltage threshold and higher photodiode sensitivity), the particular polarity of the response signal associated with infrared light can thereby be inferred, and the infrared amplitude A can be adjusted independently of the red amplitude B. This is for example useful to selectively reduce the LED drive signals, hence saving power.

The example LED driving signal 900 shown in FIG. 9 can for example be generated by:

$$\alpha \times \sin\left(\frac{t}{T0}\right) \quad (10)$$

where t is time in seconds and (in pseudo-C notation):

$$\alpha = (!(p\%16)?A:(!((p+7)\%16)?B:C \quad (11)$$

where A, B and C are the amplitudes indicated in FIG. 9, % denotes modulo operations and p is the integer half period of the signal:

$$p = integer\left(\frac{2t}{T0}\right) \quad (12)$$

An additional benefit of this scheme is that the temporal relation between driving and response signals can be established without requiring the signals to be synchronous, which makes the approach robust against spurious loss of data anywhere in the signal line.

In some embodiments, this phase shifted multiplexing scheme is used to maintain the response signal components corresponding to light from both of the light emitting diodes at substantially the same DC level by adjusting the amplitudes of the triggering peaks in the driving signal by means of a dynamic feedback system. This prevents any non-linearity in the input channel from affecting the measurements, and also reduces power consumption, as only the power needed generate sufficient response signal levels is given to the LEDs. For example, if the finger or other body part is removed from the sensor, the light will automatically dim as the feedback system compensates for the increased light transmittance. A schematic diagram of an example of such a system is shown in FIG. 11.

Figure 11:
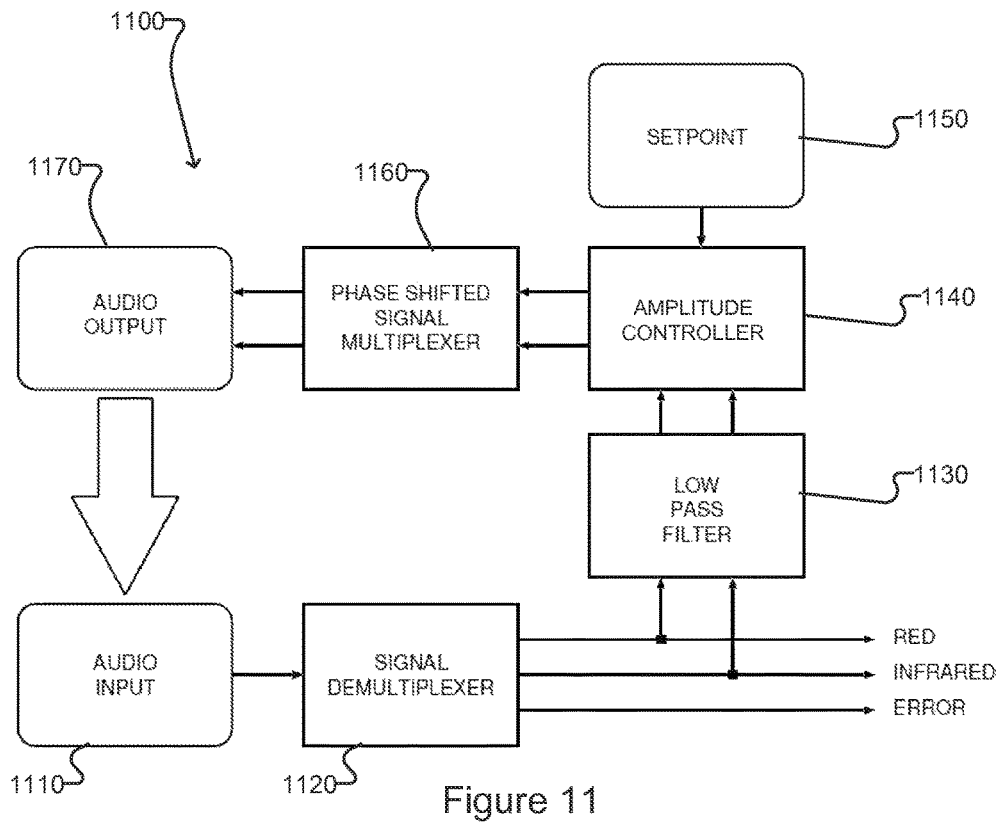
FIG. 11 schematically illustrates an example system for controlling an electronic device to operate an external sensor connectable to an audio interface of the electronic device according to one embodiment.

FIG. 11 shows an example system 1100, which constitutes the first stage of an audio based pulse oximeter according to one embodiment. The analog response signal is received at audio input 1110 and converted into a digital signal by an analog to digital converter of the electronic device (not shown), and the digital signal is provided to a signal demultiplexer 1120 that separates the interlaced channels of red and infrared signals. Demultiplexer 1120 also generates an error signal indicating whether the response signal has any unexpected characteristics. Both the red and infrared signals are provided to a low pass filter 1130. The low pass filter 1130 can be of any type known in the art, including Butterworth, elliptic, moving average or any type of filter that achieves adequate suppression of high frequency components or combinations thereof. In some embodiments the low pass filter is a fourth order Butterworth filter with a cutoff frequency of 0.5 Hz.

Figure 11A:
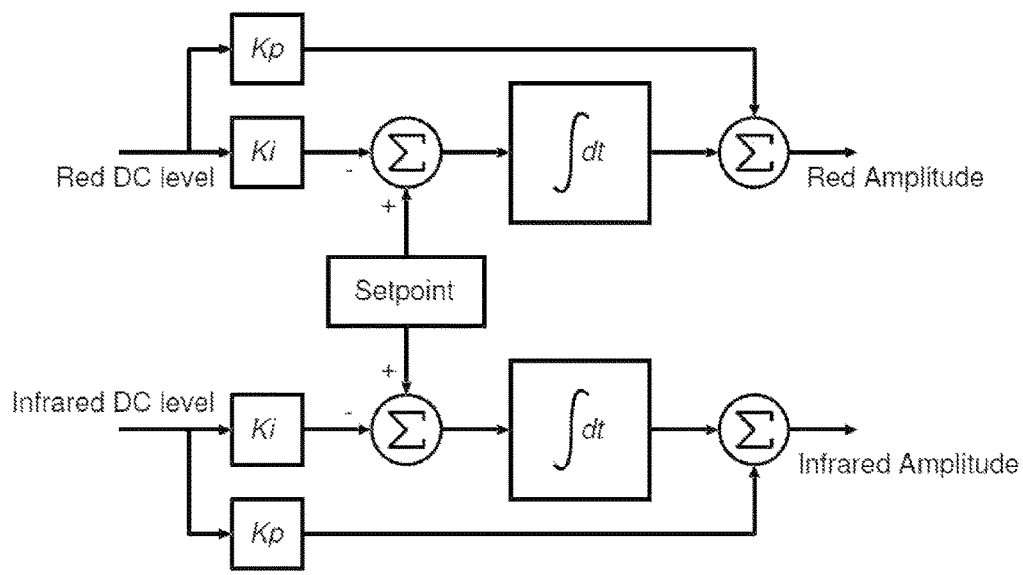
FIG. 11A schematically illustrates an example amplitude controller for determining driving signal amplitudes according to one embodiment.

The low pass filter 1130 acts to isolate the DC component of the incoming signals. This component is fed to an amplitude controller 1140 that regulates the amplitudes of the peaks in the driving signal applied to audio output 1170 such that the DC component of the incoming response signal components are adjusted based on a control setpoint 1150 provided to controller 1140. For example, in some embodiments, the DC components of the incoming response signal components are maintained within a predetermined range of setpoint 1150. The amplitudes output by controller 1140 are provided to a phase shifted signal multiplexer 1160 in order to generate the driving signal applied to audio output 1170. The controller 1140 can be implemented by any method known to those skilled in the art, such proportional-integral-derivative (PID) control, pseudo-derivative feedback (PDF) control, or combinations thereof. FIG. 11A schematically illustrates an example embodiment of a PDF-based amplitude controller, which advantageously exhibits less overshoot and smaller oscillations around the control setpoint 1150 in comparison to other types of controllers.

Figure 12:
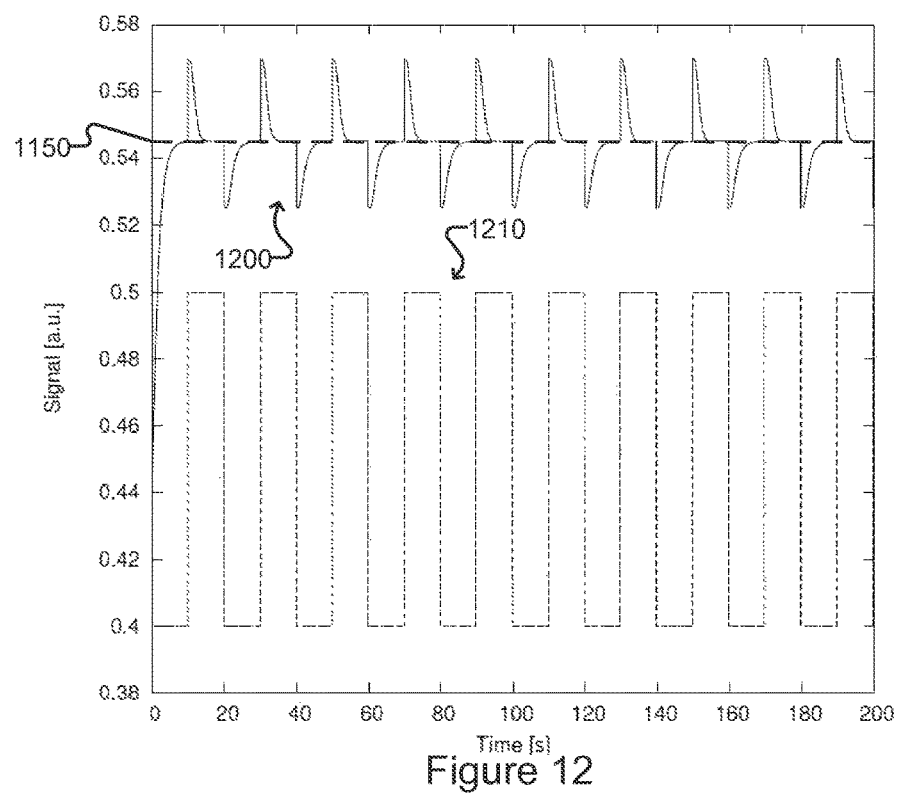
FIG. 12 is a graph illustrating the response of a controller such as the controller of FIG. 11A to a simulated disturbance.
Figure 13:
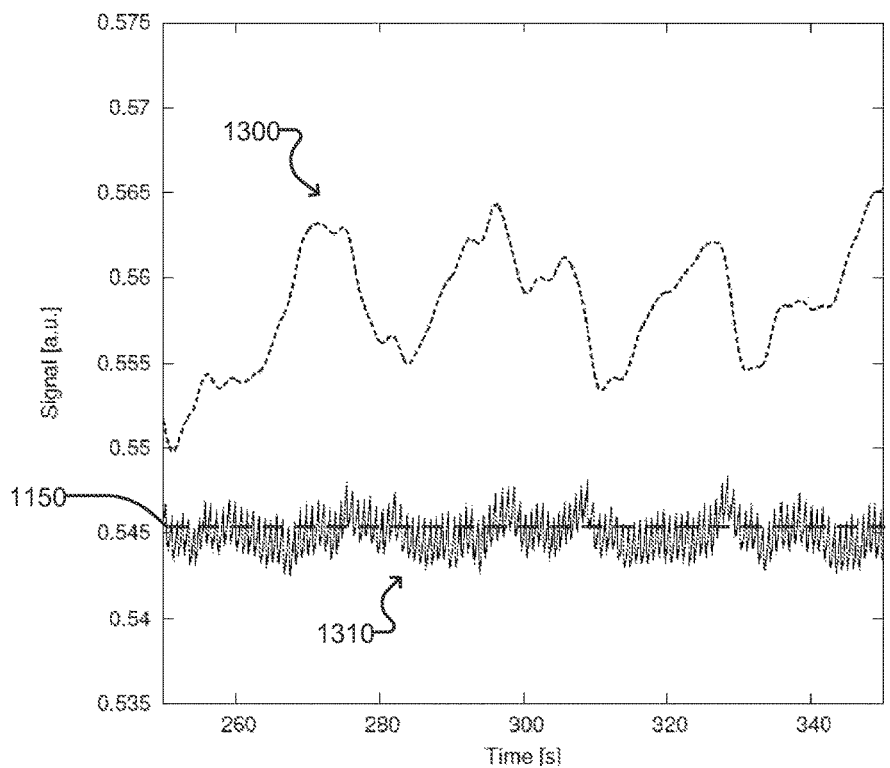
FIG. 13 is a graph illustrating an example controller response to an actual sensor response signal.

FIG. 12 shows an example controller response to a simulated disturbance. The response signal 1200 is seen to be held at the controller setpoint 1150 without oscillations or overshoot with an in-swing time of about five seconds in the presence of a significant non-continuous disturbance 1210. This is adequate for the performance of the oximeter. FIG. 13 shows an example controller response to an actual sensor signal. Trace 1300 represents the peak amplitude of the audio signal used to drive the infrared light emitting diode. The response signal 1310 can be seen to be centered at the control setpoint 1150.

Figure 14:
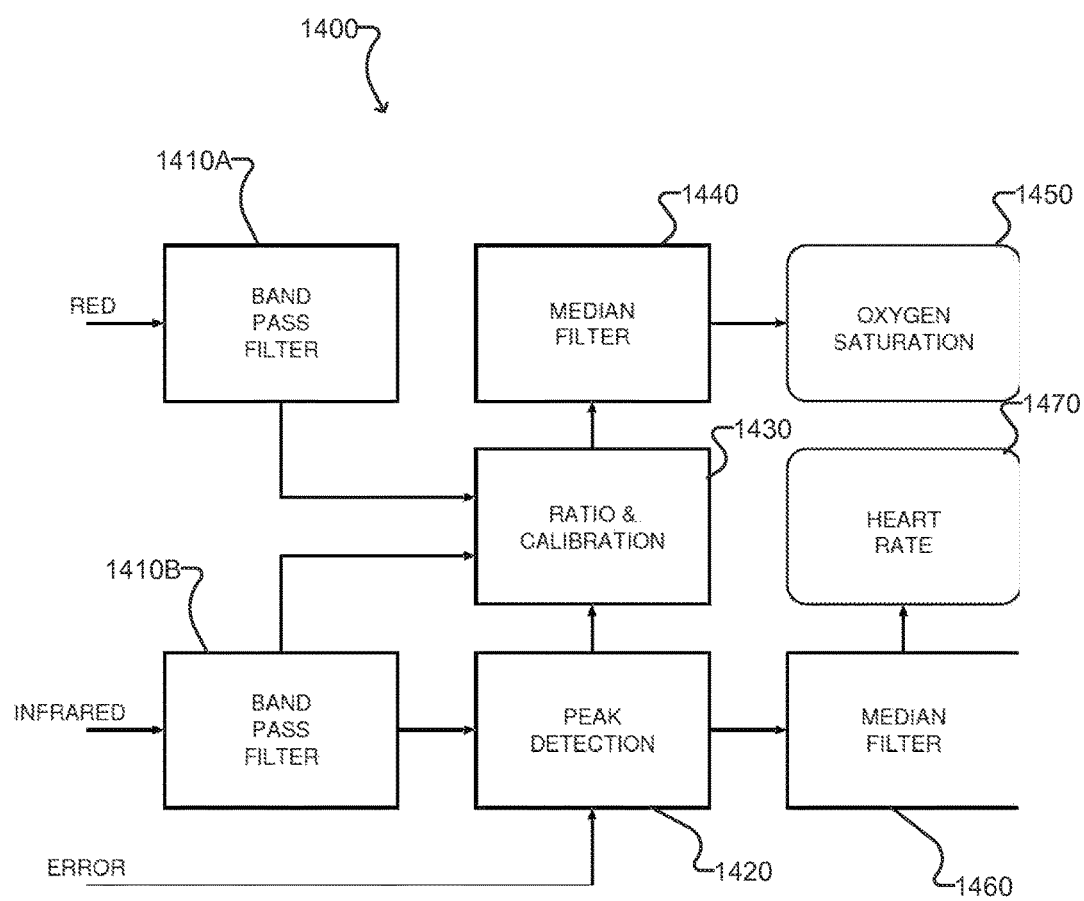
FIG. 14 schematically illustrates an example system for determining oxygen saturation and heart rate from demultiplexed response signals according to one embodiment.

The outputs of demultiplexer 1120 of system 1100 (the first oximeter stage) is passed into a second stage 1400 shown schematically in FIG. 14. This stage is responsible for calculating the heart rate and oxygen concentration. The raw input red and infrared signals are first provided to band pass filters 1410A and 1410B, respectively.

Filters 1410A and 1410B may comprise any type of filter known in the art, including Chebyshev, Elliptic, Bessel or Butterworth filters, or combinations thereof, of any order giving adequate attenuation outside the filter band. In some embodiments filters 1410A and 1410B are of the Butterworth type of the fourth order, with lower and upper cutoff frequencies of 0.5 Hz and 5 Hz respectively. The filtered infrared signal is provided to peak detection block 1420. The peak detection block may perform any peak detection algorithm known to those skilled in the art. Some embodiments use a simple level based algorithm. This is adequate since the filtered signal is well conditioned. The error signal from the first stage demultiplexer 1120 is provided to peak detection block 1420 and used as a peak validation to prevent spurious data from propagating further in the signal chain.

Peak detection block 1420 triggers the calculation of signal ratio and oxygen saturation in ratio and calibration block 1430. The conventional calculation of the oxygen saturation is to calculate the ratio R according to equation (9) above, and convert this to oxygen saturation through an empirical relationship, which is typically assumed to be linear, as follows:

$$SpO_2 = a - b \times R \tag{13}$$

where a and b are constants that are determined experimentally.

Due to the feedback provided to controller 1140 the DC level is maintained at the same level for both signal channels, the expression for R in equation (9) above reduces to a simple ratio as follows:

$$R = \frac{AC_{red}}{AC_{infrared}} \tag{14}$$

The oxygen saturation calculated at block 1430 is processed by a median filter 1440 to produce the final oximeter saturation output 1450.

The peak detection block 1420 also determines of the time between successive peaks. This time is equal to the heart rate, and is fed through a median filter 1460 to produce the heart rate output 1470.

Figure 15:
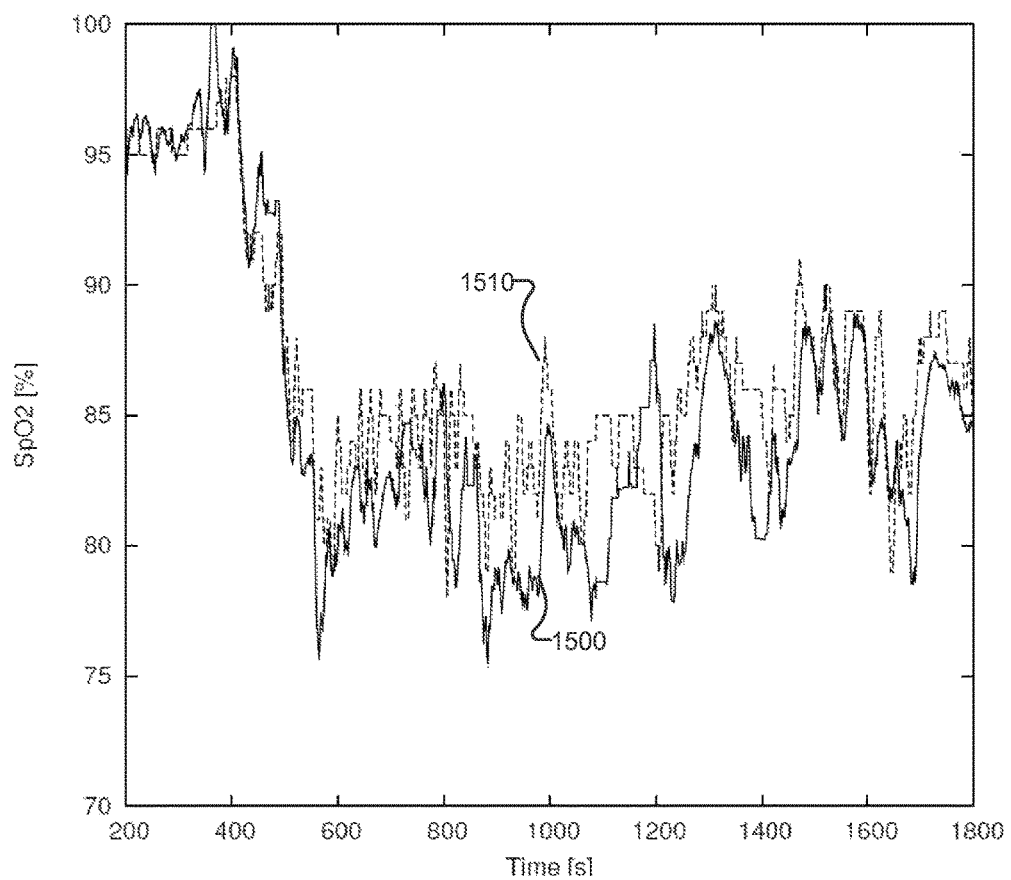
FIG. 15 is a graph illustrating a comparison between oxygen saturation readings obtained by an oximeter according to an example embodiment and a commercially available clinical oximeter.
Figure 16:
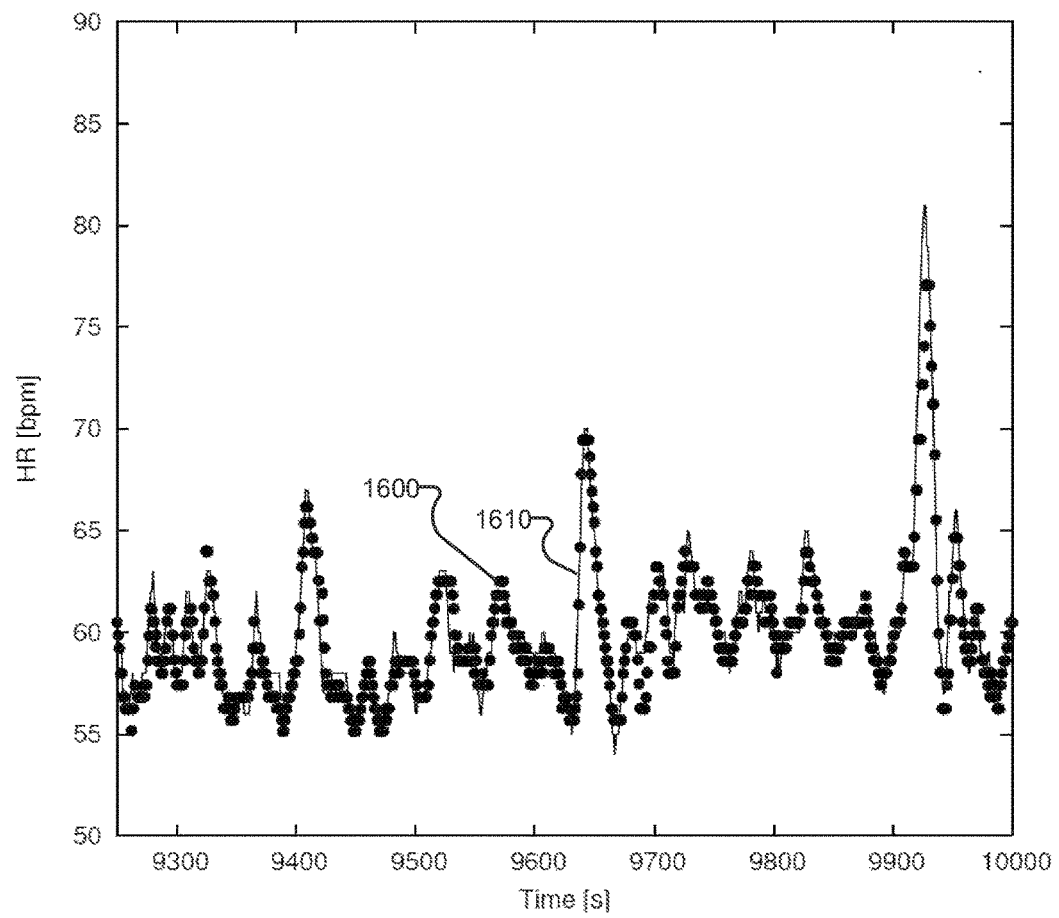
FIG. 16 is a graph illustrating a comparison between heart rate readings obtained by an oximeter according to an example embodiment and a commercially available clinical oximeter.

FIG. 15 shows a comparison between an oximeter according to an example embodiment, indicated by solid trace 1500, and a commercially available conventional clinical oximeter, indicated by dashed trace 1510. The data was obtained in a hypoxic chamber as part of a ethics board approved clinical study on consented adult subjects. FIG. 16 shows a comparison of heart rate as output by an oximeter according to an example embodiment, indicated by bullets 1600, and as output by a commercially available clinical pulse oximeter, as indicated by trace 1610.

Although example embodiments of the present invention have been described herein with the reference to the accompanying drawings, it is to be understood that the invention is not limited to those exact constructions and operations, and that various other changes and modifications may be made by one skilled in the art.

Embodiments of the invention may be implemented using specifically designed hardware, configurable hardware, programmable data processors configured by the provision of software (which may optionally comprise 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations.

Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Software and other modules may reside on servers, workstations, personal computers, tablet computers, data encoders, data decoders, PDAs, mobile phones, media players, and other devices suitable for the purposes described herein. Those skilled in the relevant art will appreciate that aspects of the system can be practised with any suitable communications, data processing, or computer system configurations, including: Internet appliances, hand-held devices (including personal digital assistants (PDAs)), wearable computers, all manner of cellular or mobile phones, multi-processor systems, microprocessor-based or programmable consumer electronics (e.g., video projectors, audio-visual receivers, displays, such as televisions, and the like), set-top boxes, network PCs, mini-computers, mainframe computers, and the like.

Where a component (e.g. a software module, processor, controller, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or steps with equivalent features, elements and/or steps; mixing and matching of features, elements and/or steps from different embodiments; combining features, elements and/or steps from embodiments as described herein with features, elements and/or steps of other technology; and/or omitting features, elements and/or steps from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole. In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art without departing from the scope, which is defined solely by the claims appended hereto.

What is claimed is:

1. A method for generating a driving signal for an oximeter sensor comprising a red LED and an infrared LED connected in parallel with opposing polarities, the method comprising:
    providing a base harmonic signal having a base amplitude less than an activation voltage of the red and infrared LEDs; and
    selectively providing periodic positive and negative triggering peaks in the base harmonic signal, the positive and negative triggering peaks having amplitudes greater than the activation voltage of the red and infrared LEDs,
    providing the base harmonic signal, including the positive and negative triggering peaks to the red LED and the infrared LED of the oximeter sensor,
    wherein the one of the positive polarity triggering peaks and negative polarity triggering peaks for triggering the infrared LED have a lower amplitude than the other one of the positive polarity triggering peaks and negative polarity triggering peaks for triggering the red LED.

* * * * *